(12) United States Patent
Dinsmoor et al.

(10) Patent No.: US 10,213,604 B2
(45) Date of Patent: Feb. 26, 2019

(54) CONTROLLING ELECTRICAL STIMULATION BASED ON EVOKED COMPOUND MUSCLE ACTION POTENTIAL

(71) Applicant: Medtronic, Inc., Minneapolis, MN (US)

(72) Inventors: David A. Dinsmoor, St. Paul, MN (US); Peng Cong, Cupertino, CA (US); Louis Vera-Portocarrero, Minneapolis, MN (US); Xin Su, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 101 days.

(21) Appl. No.: 15/097,990

(22) Filed: Apr. 13, 2016

(65) Prior Publication Data

US 2016/0303376 A1    Oct. 20, 2016

Related U.S. Application Data

(60) Provisional application No. 62/147,404, filed on Apr. 14, 2015, provisional application No. 62/147,412, filed on Apr. 14, 2015.

(51) Int. Cl.
*A61N 1/36* (2006.01)
*A61N 1/05* (2006.01)
*A61B 5/0488* (2006.01)
*A61B 5/00* (2006.01)

(52) U.S. Cl.
CPC ........ *A61N 1/36139* (2013.01); *A61B 5/0488* (2013.01); *A61B 5/4836* (2013.01); *A61N 1/0551* (2013.01); *A61N 1/36007* (2013.01)

(58) Field of Classification Search
CPC .. A61N 1/36139; A61N 1/371; A61B 5/0488; A61B 5/4836; A61B 5/486
See application file for complete search history.

(56) References Cited

U.S. PATENT DOCUMENTS

| | | |
|---|---|---|
| 4,785,813 A | 11/1988 | Petrofsky |
| 5,913,882 A | 6/1999 | King |
| 6,091,977 A | 7/2000 | Tarjan et al. |
| 6,157,861 A | 12/2000 | Faltys et al. |
| 6,324,432 B1 | 11/2001 | Rigaux et al. |
| 7,216,001 B2 | 5/2007 | Hacker et al. |
| 7,450,992 B1* | 11/2008 | Cameron ............. A61N 1/0551 607/46 |
| 8,112,155 B2 | 2/2012 | Einav et al. |

(Continued)

FOREIGN PATENT DOCUMENTS

| | | |
|---|---|---|
| EP | 0624383 A1 | 11/1994 |
| WO | 2012155188 A1 | 11/2012 |

*Primary Examiner* — Tammie K Marlen
(74) *Attorney, Agent, or Firm* — Shumaker & Sieffert, P.A.

(57) ABSTRACT

An example system includes a stimulation generator configured to deliver electrical stimulation therapy to tissue of a patient in accordance with a stimulation therapy program. The stimulation therapy program may include a set of stimulation therapy parameters. The system may include at least one sensor configured to detect a signal including an evoked compound muscle action potential (eCMAP) in response to the application of stimulation according to the stimulation therapy program. The system may also include a processor configured to adjust one or more or the stimulation therapy parameters based on the detected signal that includes the eCMAP.

28 Claims, 13 Drawing Sheets

(56) References Cited

U.S. PATENT DOCUMENTS

| | | |
|---|---|---|
| 8,323,208 B2 | 12/2012 | Davis et al. |
| 8,560,077 B2 | 10/2013 | Feinstein |
| 8,708,934 B2 | 4/2014 | Skelton et al. |
| 9,504,830 B2 * | 11/2016 | Kaula .................. A61N 1/0551 |
| 2002/0183647 A1 | 12/2002 | Gozani et al. |
| 2005/0182456 A1 | 8/2005 | Ziobro et al. |
| 2005/0216072 A1 | 9/2005 | Mahadevan-Jansen et al. |
| 2006/0276702 A1 | 12/2006 | McGinnis |
| 2007/0282217 A1 | 12/2007 | McGinnis et al. |
| 2008/0234781 A1 | 9/2008 | Einav et al. |
| 2009/0204175 A1 | 8/2009 | Zanella et al. |
| 2010/0286554 A1 | 11/2010 | Davis et al. |
| 2011/0270119 A1 | 11/2011 | Rasmussen |
| 2013/0204097 A1 | 8/2013 | Rondoni et al. |
| 2014/0243926 A1 * | 8/2014 | Carcieri ............. A61N 1/36071 607/46 |

\* cited by examiner

CONTROLLING ELECTRICAL STIMULATION BASED ON EVOKED COMPOUND MUSCLE ACTION POTENTIAL

This application claims the benefit of priority under 35 U.S.C. § 119(e) to U.S. Provisional Application Ser. No. 62/147,404, filed Apr. 14, 2015, and to U.S. Provisional Application Ser. No. 62/147,412 filed Apr. 14, 2015.

TECHNICAL FIELD

The disclosure relates to medical therapy and, more particularly, electrical stimulation.

BACKGROUND

Medical devices, including implantable medical devices (IMDs), may be used to treat a variety of medical conditions. Medical electrical stimulation devices, for example, may deliver electrical stimulation therapy to a patient via external and/or implanted electrodes. Electrical stimulation therapy may include stimulation of nerve tissue, muscle tissue, the brain, or other tissue within a patient. In some examples, an electrical stimulation device is fully implanted within the patient. For example, an implantable electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads with percutaneous lead extensions.

Medical electrical stimulators have been proposed for use to relieve a variety of symptoms or conditions such as chronic pain, tremor, Parkinson's disease, depression, epilepsy, migraines, urinary or fecal incontinence, pelvic pain, sexual dysfunction, obesity, and gastroparesis. An electrical stimulator may be configured to deliver electrical stimulation therapy via leads that include electrodes implantable proximate to the spinal cord, pelvic nerves, gastrointestinal organs, sacral nerves, peripheral nerves, or within the brain of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

SUMMARY

In general, this disclosure relates to adjusting electrical stimulation parameters associated with electrical stimulation delivered to a patient based on a detected evoked compound muscle action potential (eCMAP). The eCMAP may be evoked in response to the application of electrical stimulation therapy defined according to a set of stimulation parameters.

The eCMAP can be sensed by a sensor which is located far from the contracting muscle (i.e., a far-field eCMAP) or a sensor which is placed in, or in close proximity to, the activated muscle (i.e., a near-field eCMAP). In some examples, the sensor can be built-in with one or more stimulation electrodes. In other examples, the same electrode, or electrodes, may be configured to deliver stimulation signals and detect the eCMAP.

In some examples, a method consistent with the disclosure includes applying, via one or more electrodes, stimulation therapy to a patient according to a set of stimulation therapy parameters; detecting a signal including an evoked compound muscle action potential (eCMAP) in response to the application of the stimulation therapy; and adjusting one or more of the stimulation parameters based on the detected signal.

In some examples, the disclosure describes a system that includes a stimulation generator; one or more electrodes configured to apply stimulation therapy from the stimulation generator based on a set of stimulation therapy parameters; and a processor configured to: receive a detected signal including an evoked compound muscle action potential (eCMAP) in response to the application of the stimulation therapy; analyze the detected signal; and adjust at least one of the stimulation parameters based on the analysis of the detected signal.

In some examples, the disclosure describes a system that includes means for applying stimulation therapy to a patient according to a set of stimulation therapy parameters; means for detecting a signal including an evoked compound muscle action potential (eCMAP) in response to the application of the stimulation therapy; and means for adjusting one or more of the stimulation parameters based on the detected signal.

The details of one or more examples are set forth in the accompanying drawings and the description below. Other features, objects, and advantages will be apparent from the description and drawings, and from the claims.

DETAILED DESCRIPTION

Figure 1:
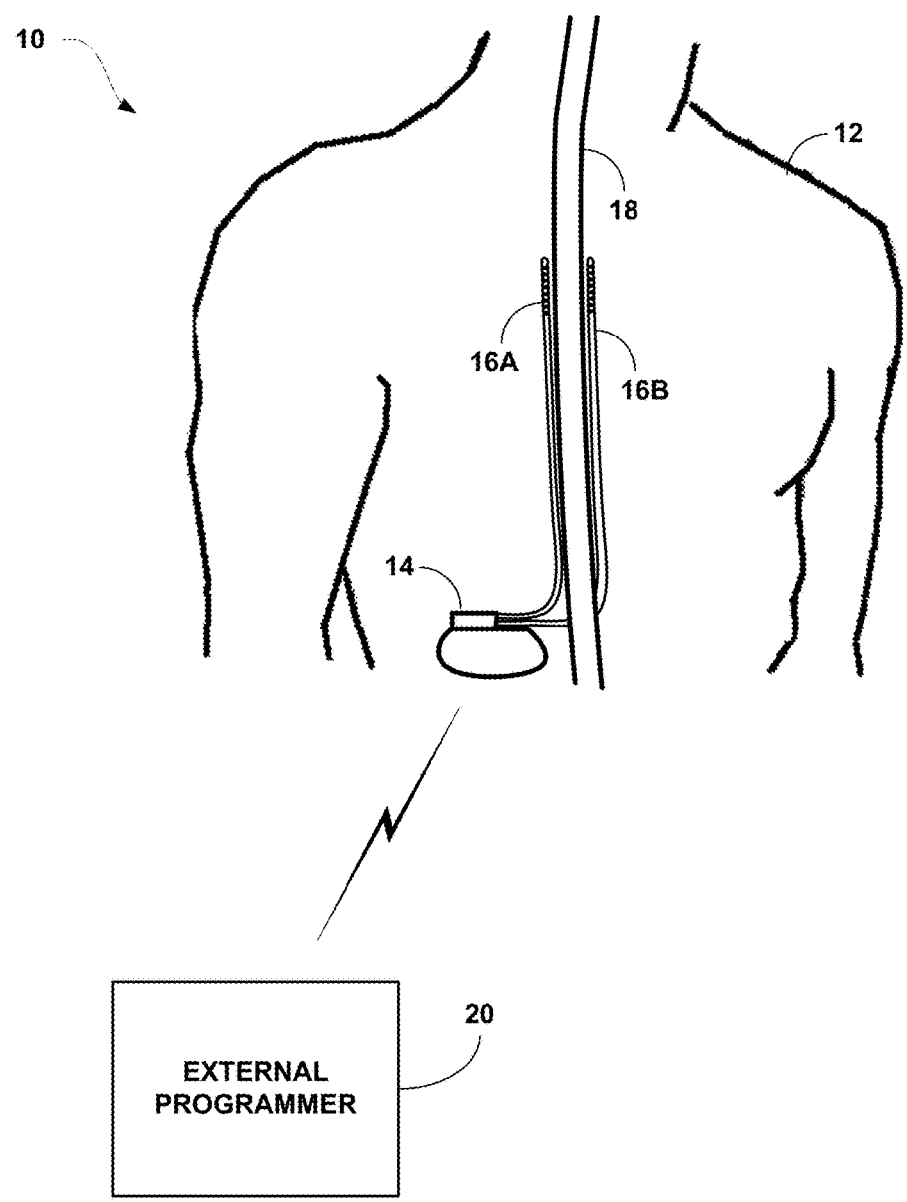
FIG. 1 is a schematic diagram illustrating an example implantable stimulation system including a pair of implantable stimulation electrode arrays carried by implantable leads.

This disclosure includes systems, devices, and methods relating to adjusting electrical stimulation parameters that define electrical stimulation delivered to a patient. A patient may receive electrical stimulation therapy to relieve a variety of symptoms or conditions. In some cases, a physician or clinician may manually adjust electrical stimulation parameters according to patient feedback such as the patient's perception on reduction in pain levels or any changes in symptoms. However, patient feedback can be inconsistent over time and it is also subjective. In this manner, it may be difficult to determine the most appropriate stimulation parameters to relive the patient's symptoms or conditions and provide improved system performance (e.g., efficient energy usage and targeted therapy delivery).

As discussed herein, systems and methods are described for adjusting electrical stimulation parameters based on a detected evoked compound muscle action potential (eCMAP). The eCMAP may be evoked in response to the application of electrical stimulation therapy that is defined according to a set of stimulation parameters. Adjustments to the electrical stimulation parameters based on the detected eCMAP may provide more objective information than patient feedback. In addition, eCMAP detection may allow a system to provide closed-loop stimulation control. Incorporation of eCMAP into adjustment, and/or titration, of stimulation parameters may allow for stimulation systems to provide stimulation therapy that uses less energy, more targeted stimulation delivery to desired tissues, and/or improved therapeutic efficacy as compared to techniques that do not incorporate eCMAP detection.

In some examples, dorsal column stimulation therapy or other electrical stimulation therapy is provided according to a therapy program with stimulation parameters, such as current or voltage amplitude, frequency, and/or pulse width, that are selected to be just on the verge of triggering a response in muscle fibers innervated by motor neurons activated by the stimulation therapy. The activation of the motor neuron may be indirect through an intermediary such as an interneuron. One example muscle group which may activate during therapeutically optimized neurostimulation is the group of paraspinal muscles. Although the triggered muscle response may be electrically detectable, the resultant activation may go unnoticed by the patient receiving therapy. When a motor neuron is stimulated above the muscle activation threshold, the aggregate electrical response generated by the muscles following the excitation is referred to as an evoked compound muscle action potential (eCMAP). The eCMAP may be detected by an electrical sensing system such as one within an implantable medical device, or in electrical communication with said device. The sensing system may include one or more electrodes positioned at some distance away from the muscle. In such examples, the sensing is deemed "far-field" owing to the fact that the electrical field generated by the activated muscle originates from a point remote from the sensor. This far-field sensing paradigm is similar to the effect noted in dual-chamber cardiac pacemakers, whereby a sensing electrode placed in the right atrial appendage may sense the electrical signal resulting from ventricular activation despite being physically distant from the ventricle. In other examples an eCMAP biomarker may be detected by biosensors directly in a patient's muscles or dermatomes at approximately the same location as being activated by the delivered stimulation. The location may be considered a target location. In some examples, eCMAP biomarker in biosensor at the target location may be a near-field eCMAP biomarker.

In some examples, detection, or the lack thereof, of the presence of the eCMAP in response to stimulation provided at a particular set of therapy parameters is used to program initial stimulation therapy parameters provided to a patient via an implantable medical device. In other examples, the detection of eCMAP in response to stimulation provided at a particular set of therapy parameters may be used to adjust existing stimulation therapy parameters. The programming or adjustment of stimulation therapy parameters may be manual or automatic. The presence or absence of an eCMAP in response to a set of stimulation therapy program may be used as a biomarker in programing and adjustment to patient stimulation. For example, during initial programming, an IMD may start providing stimulation according to an initial therapy parameter set. If there is not eCMAP biomarker detected, the IMD may increase the total intensity of the stimulation. The intensity of the stimulation may be increased, for example, by increasing the amplitude, frequency and/or pulse width of stimulation pulses. In some examples, the stimulation intensity may be increased at predetermined increments until an eCMAP biomarker is detected. If the detected eCMAP biomarker indicates that the stimulation is affecting the wrong location, the IMD may adjust the electrode combination through which stimulation is applied. If the stimulation is activating neurons in the appropriate location, IMD may adjust the stimulation parameters to provide a desired eCMAP biomarker.

In some examples, stimulation above a particular intensity may cause muscle fibers innervated by nerves stimulated with the electrical stimulation therapy to be activated along with the target nerves. The activation of the muscle fibers gives rise to an eCMAP biomarker which may be detected by one or more sensors. The location of the eCMAP biomarker in response to stimulation allows the IMD to determine whether the stimulation therapy is activating neurons in the intended area. However, activation of muscle fibers may be an undesirable side effect of stimulation therapy. In some examples, as the amplitude of the eCMAP biomarker increases, the larger the number of muscle fibers being activated. A large number of muscle fibers activated in a given area may give rise to a feeling of muscles twitching in the patient. In order to avoid this potentially undesirable side effect, an IMD may adjust stimulation parameters to minimize the muscle activation felt by the patient. In some examples, the stimulation parameters may be adjusted until the amplitude of the eCMAP biomarker is below a threshold level. In some examples, the stimulation parameters are adjusted until the eCMAP biomarker has just disappeared.

In some examples, during programming, the IMD measures and saves the eCMAP biomarker for a variety of stimulation parameter combinations, i.e., combinations of amplitude, frequency and/or pulse width. For example, the memory of IMD may store a set of stimulation parameters along with the amplitude of the eCMAP in response to the stimulation as well as the time between the application of the stimulation and the detection of the eCMAP in response to the stimulation. In some examples, the amplitude of the eCMAP biomarker and/or the time between the application of the stimulation and the detection of the eCMAP may be compared to previously stored values to determine if there has been a shift in the location of one or more electrodes providing the stimulation. In some examples, the eCMAP biomarker may be detected by a device other than the IMD providing stimulation.

In some examples, the IMD may use a detected eCMAP biomarker to determine whether the patient's response to a particular set of stimulation parameters has changed. In some examples, the IMD detects eCMAP in response to a current stimulation therapy program on an ongoing basis. For example, eCMAP biomarker may be detected every few seconds, once a minute, once every few minutes, hourly, daily or weekly. In some examples, an eCMAP biomarker may be detected in response to a change in another sensed physiological parameter. For example, the IMD may detect an eCMAP biomarker when there has been a change in activity level or posture of the patient.

The detected change in eCMAP biomarker may be, for example, a change in the effectiveness of the stimulation parameters, which may be detected in the amplitude of the eCMAP in response to the stimulation, or a change in the location of activation, which may also be determined from the time between application of the stimulation and receipt of the eCMAP. In some examples, the IMD compares a currently detected eCMAP in response to a particular stimulation therapy program to a previously saved eCMAP in response to the same stimulation therapy program. If a change in the eCMAP in response to the stimulation program is detected, the IMD may adjust one or more of the stimulation parameters associated with the stimulation therapy program. The IMD may make adjustments in an iterative manner until an eCMAP in response to stimulation parameters is approximately equal to the desired eCMAP. In some examples, the desired eCMAP is the eCMAP previously saved in association with the stimulation therapy program being adjusted. In some examples, the desired eCMAP biomarker is saved during programming in response to patient 12 indicating that the current stimulation parameters provide efficacious therapy. In some examples, IMD 14 may store multiple desired eCMAP biomarkers, each associated with a different patient state in which patient 12 indicated efficacious therapy was being delivered. In some examples, after the desired eCMAP biomarker is achieved, the new stimulation parameters may replace the old stimulation parameters in the stimulation therapy program. In some examples, the new stimulation parameters may be stored in a new stimulation therapy program along with one or more changes in other sensed signals detected along with the change in the eCMAP biomarker. For example, the new stimulation therapy program may be stored in association with a patient status such as activity level or posture state.

In general, evoked compound muscle action potential (eCMAP) is a measure of a muscular response signal generated by the aggregate activity of a group of muscle tissues firing in response to an externally applied electrical stimulation, generally but not limited to electrical stimulation provided to a human patient. In contrast to an eCMAP signal, an eCAP signal is a measure of the aggregate (compound) neural activity of a group of nerves firing in conjunction with each other. An eCAP signal is generally detectable at a time period after application of electrical stimulation that is earlier than the time period when an eCMAP signal generated in response to the same electrical stimulation would be detectable. In addition, the eCMAP signal is a signal that can be sensed within the patient by sensors that are not necessarily located in the same location where the stimulation that caused the eCMAP signal to occur was delivered. The sensors detecting the eCMAP signal also may not be in intimate contact with the muscle tissue or with a location where the electrical stimulation was applied. This ability to sense the eCMAP signal in a location other than were the stimulation was applied is referred to as "far-field" signal detection. An example of far-field detection of an eCMAP signal includes instances where stimulation is applied to the spinal cord (e.g., wherein the electrodes providing the stimulation are located within the epidural fluid of the spinal cord) and the eCMAP signal generated in response to the stimulation applied to the spinal cord is sensed at the para-spinal muscles located outside the bony structure of spinal cord. In another example of far-field detection, electrical stimulation is applied using sacral leads implanted in the fatty matter of the sacrum and an eCMAP signal generated by the muscle tissue of the levator ani is detected by sensors located in the pelvic floor of a patient. Generation of an eCMAP signal by a group of muscle tissue can occur in response to applied stimulation without resulting in an actual contraction of the muscle tissue generating the eCMAP signal. In other words, a patient may not even perceive muscle activity indicated by an eCMAP signal if no muscle contraction occurs. In various examples, detecting an eCMAP signal may thus include detecting an eCMAP signal generated by a group of muscle tissue without having the muscles tissue being stimulated to a level that causes actual muscle contraction of the muscle tissue to occur. The eCMAP signal may thus provide more accurate indications of muscles affected by a delivered stimulation signal. Further, eCMAP signals are detectable when a patient is sedated, wherein other signals such as eCAP or EMG may be less easily detectable in sedated patients.

An electromyography (EMG) signal is a signal indicative of electrical activity generated by muscle tissue, generally related to a specific muscle or muscle group. An EMG signal is generally sensed by electrodes or other sensors implanted into or directly in contact with the muscle tissue generating the EMG signal. In addition, an EMG signal is typically indicative of the intrinsic activity generated by muscles and is targeted to a specific muscle or muscle group. In this manner, an EMG signal is not necessarily generated or evoked in response to an externally applied electrical stimulation, but can be a result of the patient's own conscious or unconscious stimulation of the muscle tissue. An eCMAP signal on the other hand is an evoked response generated in response to externally applied electrical stimulation. In general, the eCMAP signal is not specific to the targeted muscle tissue or muscle group where the externally applied electrical stimulation has been applied, and the eCMAP signal can be sensed as a far-field signal at a location in or on the patient at some distance from the location where the electrical stimulation was applied.

FIG. 1 is a schematic diagram illustrating an example implantable stimulation system 10 including a pair of implantable electrode arrays in the form of stimulation leads 16A and 16B. Although the techniques described in this disclosure may be generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable spinal cord stimulation (SCS) system for purposes of illustration, but without limitation as to other types of medical devices.

As shown in FIG. 1, system 10 includes an IMD 14 and external programmer 20 shown in conjunction with a patient 12. In the example of FIG. 1, IMD 14 is an implantable electrical stimulator configured for spinal cord stimulation (SCS), e.g., for relief of chronic pain or other symptoms. Again, although FIG. 1 shows an implantable medical device, other embodiments may include an external stimulator, e.g., with percutaneously implanted leads, or implanted leads with percutaneous lead extensions. Stimulation energy is delivered from IMD 14 to spinal cord 18 of patient 12 via one or more electrodes disposed on implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1 is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, or gastroparesis. In this manner, system 10 may be configured to provide therapy taking the form of deep brain stimulation (DBS), pelvic floor stimulation, gastric stimulation, or any other stimulation therapy. In addition, patient 12 is ordinarily a human patient.

Each of leads 16 may include electrodes and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as dosage amount, rate, or the like for drug delivery.

In the example of FIG. 1, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation that used on a temporary basis to evaluate potential efficacy to aid in consideration of chronic implantation for a patient. In additional embodiments, IMD 14 may be a leadless stimulator with one or more arrays of electrodes arranged on a housing of the stimulator rather than leads that extend from the housing.

The stimulation may be delivered via selected combinations of electrodes carried by one or both of leads 16, e.g., in bipolar, unipolar, or multipolar combinations. The target tissue may be any tissue affected by electrical stimulation energy, such as electrical stimulation pulses or waveforms. Such tissue includes nerves, smooth muscle, and skeletal muscle. In the example illustrated by FIG. 1, the target tissue is spinal cord 18. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead. Other electrode and lead configurations may be adapted for use with the present disclosure so long as they enable IMD 14 to electrically stimulate and sense from a target tissue.

In the example of FIG. 1, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), sacral neuromodulation (SNM), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 may deliver stimulation therapy according to one or more programs. A program defines one or more parameters that define an aspect of the therapy delivered by IMD 14 according to that program. For example, a program that controls delivery of stimulation by IMD 14 in the form of pulses may define a voltage or current pulse amplitude, a pulse width, and a pulse rate, for stimulation pulses delivered by IMD 14 according to that program. The program may also define an electrode combination for delivery of the stimulation pulse, including electrode polarities. Moreover, therapy may be delivered according to multiple programs, wherein multiple programs are contained within each of a multiple of groups.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. Stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may be decreased to avoid causing patient 12 additional pain or unusual sensations, which may be considered undesirable side effects that undermine overall efficacy.

Also, posture state changes may present changes in symptoms or symptom levels, e.g., pain level. Reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 may include a posture state module that detects the posture state of patient 12 and causes the IMD 14 to automatically detect an eCMAP in response to stimulation in response to a change in posture state. Based on the detected eCMAP, IMD 14 determines whether an adjustment to the stimulation parameters is recommended or otherwise appropriate. For example, a posture state module may include a posture state sensor, such as an accelerometer, that detects when patient 12 lies down, stands up, or otherwise changes posture.

A posture state module may include, for example, one or more accelerometers that detect when patient 12 occupies a posture state in which it may be appropriate to decrease the stimulation amplitude, e.g., when patient 12 lies down. In some examples, the IMD may automatically reduce stimulation amplitude so that patient 12 does not manually have to do so. The IMD may then detect an eCMAP biomarker in response to the adjusted stimulation parameters to determine if the adjustment was effective. In other examples, the IMD may detect an eCMAP biomarker in response to stimulation when a change in posture is detected prior to making an adjustment to the stimulation parameters. IMD 14 may analyze the detected eCMAP biomarker to determine the appropriate adjustment to the stimulation parameters. Example posture states may include "Upright," "Upright and Active," "Lying Down," and so forth.

As will be described in greater detail below, in some examples, IMD 14 may be configured to automatically adjust stimulation amplitude when it detects that patient 12 has changed position. In some examples, in response to detection of a change in position, IMD 14 determines an appropriate adjustment to the stimulation parameters. In some examples, the determination may include detecting an evoked compound muscle action potential (eCMAP) based on the current stimulation parameters, and making adjustments to one or more stimulation parameters based on the eCMAP biomarker detected. In other examples, IMD 14 may select a new set of stimulation parameters stored in a memory based on previously detected eCMAP for the same position.

In some examples, stimulation parameter may be configured to be change at a rate suitable to prevent undesirable effects, e.g., such as the effects due to the compression of leads 16 towards spinal cord 18 when patient 12 lies down. In some examples, IMD 14 may be configured to decrease the stimulation amplitude to a first predetermined lower amplitude value substantially immediately upon detection by IMD 14 that patient 12 is lying down. IMD 14 may then evaluate the appropriateness of the new stimulation amplitude based on eCMAP, and make further adjustments as necessary. In other examples, IMD 14 may be configured to detect an eCMAP biomarker to stimulation upon detection of patient 12 lying down. Based on the detected eCMAP biomarker, IMD 14 may adjust one or more stimulation parameters until a desired eCMAP biomarker is achieved.

In response to a posture state indication by the posture state module, IMD 14 may change a program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. The amount of automatic reduction may be determined, at least in part, based on a detected ECMAP biomarker in the new posture state. In some cases, IMD 14 may communicate with external programmer 20 to present a proposed change in stimulation in response to a posture state change, for example for a first posture state to a second posture state, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

In some examples, IMD 14 may periodically detect eCMAP generated in response to current stimulation parameters and adjust the current stimulation parameters if there has been a significant change, i.e., greater than a predetermined threshold change, to the detected eCMAP biomarker relative to a desired or reference eCMAP biomarker. IMD 14 may detect and analyze eCMAP on an hourly, daily, weekly, or monthly basis for example. In some examples, IMD 14 may initiate an eCMAP biomarker detection and analysis cycle if a predetermined amount of time has passed since the last eCMAP biomarker detection. The time may reset any time an eCMAP biomarker is detected.

Referring still to FIG. 1, a user, such as a clinician or patient 12, may interact with a user interface of external programmer 20 to program IMD 14. The user interface may include an output device for presentation of information, and an input device to receive user input. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A program group may be characterized by multiple programs that are delivered simultaneously or on an interleaved or rotating basis.

During the delivery of stimulation therapy, patient 12 may make patient therapy adjustments, i.e., patient adjustments to one or more parameters of a therapy via an input device of a user interface of a programmer, to customize the therapy either after patient 12 moves to a different posture state or in anticipation of the next posture state. In some examples, IMD 14 may detect an eCMAP in response to the therapy adjustment. In some examples, the detected eCMAP in response to the adjusted therapy may be stored as indicating effective therapy for a particular patient state. If the same patient state is detected again, IMD may automatically adjust one or more stimulation parameters in order to achieve an eCMAP biomarker which corresponds to the stored eCMAP biomarker. In examples where IMD 14 is in a record mode to store all patient therapy adjustments associated with a specific patient state, IMD 14 may implement a method to ensure that patient therapy adjustments are associated with the correct patient state intended by patient 12 when the therapy adjustment was made. The patient 12 may occupy the patient state multiple times such that there are multiple instances of the sensed patient state. A patient state may be a posture or activity level, for example. In some examples, each time the patient 12 occupies a posture state, the patient may enter one or more therapy adjustments.

In some cases, external programmer 20 may be characterized as a physician or clinician programmer if it is primarily intended for use by a physician or clinician. In other cases, external programmer 20 may be characterized as a patient programmer if it is primarily intended for use by a patient, e.g., for entry of patient input to specify patient adjustments to one or more therapy parameters. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use, either manually or via other user input media.

External programmer 20 may present eCMAP biomarker data stored in IMD 14 from the detected eCMAP biomarkers to various patient states of patient 12. The eCMAP data may be acquired by external programmer 20 from IMD 14 to generate patient state information, e.g., changes in eCMAP biomarker and associated therapy adjustment. IMD 14 may also store any associations between changes in eCMAP response, therapy adjustments, and the patient states for which the therapy adjustments were intended during a record mode, i.e., therapy adjustment information. By recording all therapy adjustments made for a program in each of the patient states, including each of the multiple instances of the sensed patient states, external programmer 20 may be able to present therapy adjustment information to the user that indicates a desired eCMAP biomarker and corresponding stimulation parameters based upon parameter use. For example, the user may be able to identify the most recent stimulation parameters desired by patient 12, the minimum and maximum allowable amplitudes, or even the quantified number of therapy adjustments to indicate that patient 12 is either satisfied with a program or cannot readily find suitable parameters for a program with many therapy adjustments.

The therapy adjustment information stored during the record mode may be presented in any number of different manners. For example, an output device of the user interface may present each program of a group and the respective number of therapy adjustments and the range of such amplitudes defined by the therapy adjustments. Alternatively, an output device of the user interface may also, or instead, present the last (i.e., most recent) amplitude used by patient 12 to deliver therapy with each program. In any manner, the therapy adjustment information may be presented in a graphical, numerical, or textual mode on external programmer 20. The user may be able to customize the presentation of the therapy adjustment information in other examples.

In some examples, external programmer 20 may utilize the associations of the eCMAP biomarker and the therapy adjustments, to posture states in order to further minimize time needed to program all therapy programs. When presenting the amplitude ranges of the therapy adjustments for each therapy program, the user may be able to provide a single confirmation input that sets the amplitude for all programs to some nominal therapy parameter, for example. The nominal therapy parameter may be a minimum amplitude associated with the program and posture state, the last amplitude associated with the program and posture state, or some other therapy parameter already stored by IMD 14 in association with each therapy program and posture state. The therapy parameter may be referred to as nominal in the sense that it refers to a parameter value by a name that is descriptive of the value, rather than to a specific, absolute parameter value. In cases where a program has not been associated with any therapy adjustment, no new stimulation parameter may be programmed to the program.

In other examples, external programmer 20 may generate a suggested therapy parameter based upon an eCMAP biomarker to current stimulation therapy parameters and a guided algorithm. In some examples, the current stimulation therapy parameters may be a base stimulation therapy program. The suggested therapy parameter may be a specific therapy parameter value that is visible to the user, but is signified as being suggested by the guided algorithm. The guided algorithm may be an equation, set of equations, look-up table, or other technique for generating a suggested therapy parameter that may define stimulation therapy effective to patient 12. In this manner, external programmer 20 analyzes the eCMAP biomarker to previous therapy adjustments for the most appropriate stimulation parameters that fit the desires of the user. The guided algorithm may generate a low or high weighted average, a safe average that minimizes the chances of overstimulation, a trend target that weights more recent patient adjustments to therapy greater than older therapy adjustments, or even an intergroup average that looks to therapy adjustments to programs in different groups that provide stimulation therapy. In any case, the user may be able to program the plurality of programs with each suggested therapy parameter with the selection of a single confirmation input.

IMD 14 may be constructed with a biocompatible housing, such as titanium or stainless steel, or a polymeric material such as silicone or polyurethane, and surgically implanted at a site in patient 12 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

At the distal tips of leads 16 are one or more electrodes that transfer the electrical stimulation from the lead to the tissue. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Figure 2:
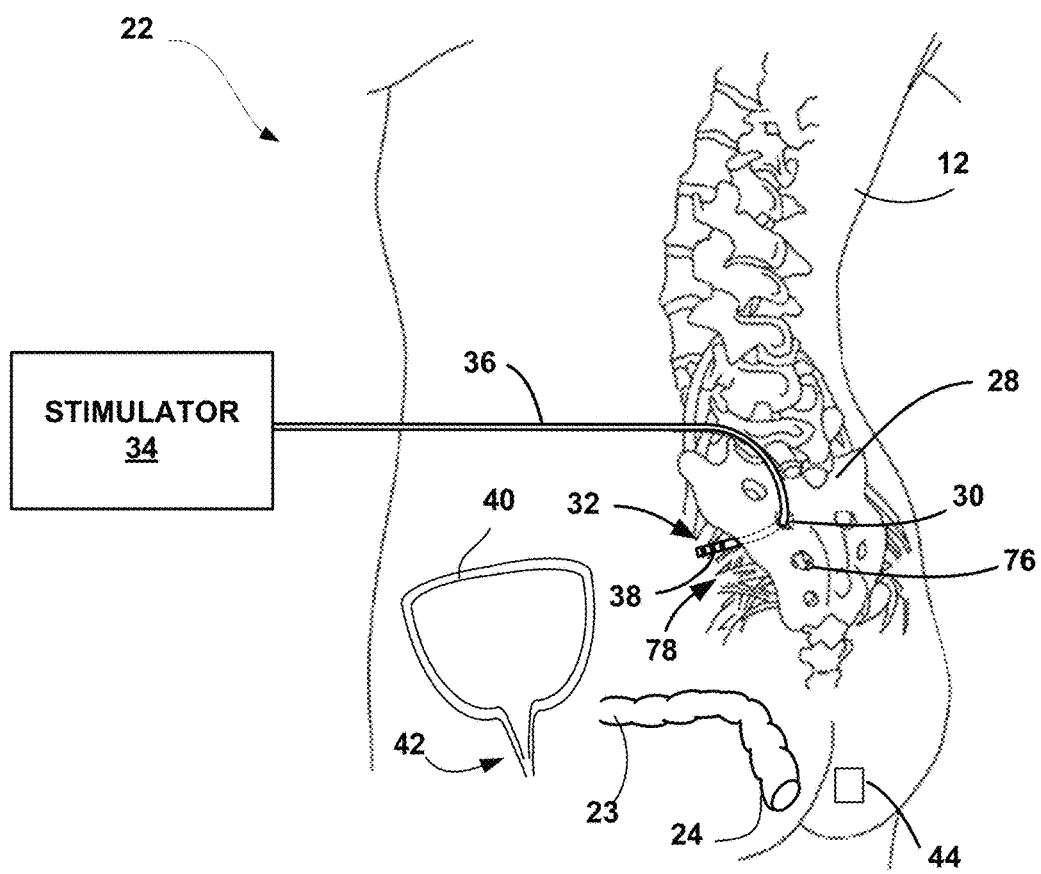
FIG. 2 is a conceptual diagram illustrating an example system that is configured to deliver sacral neuromodulation to a patient.

FIG. 2 is a conceptual diagram illustrating an example system 22 that is configured to deliver sacral neuromodulation to patient 12. As shown in FIG. 2, system 22 includes stimulator 34 (e.g., and electrical stimulator or IMD) coupled to a medical lead 36 carrying electrodes 38 near a distal end of lead 36. System 22 may also include an optional electrode patch 44. In examples where stimulator 34 is external, lead 36 may be connected to a lead extension (not shown) passing through the skin and coupled to stimulator 34. Stimulator 34 may deliver electrical stimulation at least partially defined by a set of therapy parameter values (e.g., current amplitude, voltage amplitude, pulse width, pulse frequency, and electrode combination). Although a single lead 36 is shown, two or more leads may be used in other examples.

For example, system 22 may include a second lead in order to provide bilateral neuromodulation. Bilateral neuromodulation may be provided alternatively or simultaneously depending upon the symptoms or disease being treated. For example, a stimulation pulse may be applied on both sides of the midline at the same time. In other examples, stimulation may be provided by first one lead to one side, and then by the other lead, to the other side. In some examples, the intensities of stimulation applied by each lead or for each nerve may be adjusted individually based on an eCMAP response to stimulation from each lead, or to each nerve.

Stimulator 34 may include a therapy delivery module and/or other components configured to deliver, via lead 36 and one or more electrodes 38, electrical stimulation to a sacral nerve 32 that may potentially provide therapy to control fecal or urinary incontinence, for example. Fecal incontinence may refer to a condition of involuntary loss of fecal matter, and may include urge incontinence, stress incontinence, or both stress and urge incontinence, which may be referred to as mixed incontinence. As used in this disclosure, the term "fecal incontinence" includes disorders in which fecal matter is voided (i.e., defecation) when not desired, such as stress or urge incontinence, and disorders in which fecal voiding does not occur as desired, such as irritable bowel syndrome. Urinary incontinency may refer to a condition of loss of bladder control, and may include urge incontinence, stress incontinence, or both stress and urge incontinence, which may be referred to as mixed incontinence. As used in this disclosure, the term "urinary incontinence" includes disorders in which urine is voided when not desired, such as stress or urge incontinence, and disorders in which urinary voiding does not occur as desired, such as diabetes. Similar to fecal incontinence, urinary incontinence or other pelvic floor disorders (e.g., sexual dysfunction) may also result from a lack of voluntary control and may be treated with electrical stimulation, pharmaceuticals, or other therapies. In some examples where stimulator 34 is used to treat fecal incontinence, stimulation may be applied to the second sacral nerve. In some examples where stimulator 34 is used to treat urinary incontinence, stimulation may be delivered to the third sacral nerve. Although discussed with respect to therapy for bladder and bowel dysfunctions, system 22 may be used to treat other pelvic floor conditions, to provide peripheral nerve simulation for chronic pain or sexual dysfunction, or other treatments based on stimulation applied to one or more sacral nerves.

Although only two electrodes 38 are shown on lead 36, system 22 may include three or more electrodes in other examples. In addition, electrodes 38 may be implantable or at least partially implantable in other examples. For example, lead 36 may be transcutaneous or electrodes 38 may be part of a fully implantable device for sensing and monitoring eCMAP signals. In examples, including two leads, each lead may include two or more electrodes. In some examples, one electrode may be used for sensing, while another is used for providing simulation. The electrodes may be on the same lead or on different leads. Stimulation may be provided ipsilaterally or contralaterally.

Patient 12 includes intestines 23 that may be subject to a condition such as fecal incontinence. Intestines 23 may include a descending colon, a sigmoid colon, rectum 24 and an anus. During normal, or healthy function of intestines 23, the sigmoid colon and rectum 24 are depicted such that their position relative to one another form a "valve" or "fold" that prevents fecal matter from entering rectum 24. During a fecal voiding event, however the sigmoid colon and rectum 24 may shift to positions that open the value or fold thereby allowing fecal matter in the sigmoid colon to pass to rectum 24 and exit the anus. When fecal matter is present in the sigmoid colon or rectum 24, patient 12 may typically recognize the sensation and take action (e.g., prevent fecal voiding or voluntarily void the fecal matter). However, for a patient with fecal incontinence, patient 12 may not recognize the sensation of fecal matter or be able to voluntarily control the need to void.

Although fecal incontinence may be caused by muscular or neurological dysfunction, sensations and stimulation of pelvic floor nerves and/or sensed far-field eCMAP signals may still be useful for identifying therapies that may be effective in treating the condition of patient 12. For example, far-field eCMAP signals may be detected by electrodes 38 indicating that muscles in the area near rectum 24 are being activated by applied stimulation. In some examples, far-field eCMAP signals may be detected during initial programming of SNM device such as the one in system 22. For example, stimulation intensity may be slowly raised, e.g., by adjusting one or more of voltage or current amplitude, pulse width or pulse rate, until an eCMAP biomarker is first detected. Ongoing stimulation therapy is then provided by stimulator 34 at an intensity level below the level which resulted in an eCMAP biomarker. In some examples, the stimulation intensity may be set to 50%, 80%, or 90% of the stimulation intensity resulting in the far-field eCMAP biomarker, for example. If voltage or current pulse amplitude is adjusted, for example, the amplitude may be set to 50%, 80%, or 90% of the amplitude that resulted in the far-field eCMAP biomarker.

In some examples, the set of therapy parameter values selected for electrical stimulation to treat fecal incontinence may include pulses delivered at a certain frequency. For example, if stimulation comprises delivery of pulses, the pulse frequency may be selected from a range between 0.05 Hz and 50 Hz. In another example, the pulse frequency may be selected from a range between 0.1 Hz and 25 Hz. In still another example, the pulse frequency may be selected from a range between 0.5 Hz and 15 Hz. In one example, the pulse frequency may be selected from between approximately 1.0 and 3.0 Hz. These frequencies may elicit cortical evoked potentials and therapy related to fecal incontinence. However, these frequencies may also be effective in treating other disorders such as urinary incontinence or sexual dysfunction.

Stimulator 34 may also include a therapy delivery module and/or other components configured to deliver, via lead 36 and one or more electrodes 38, electrical stimulation to second sacral nerve 32 (i.e., S2) or other nerve that may potentially provide therapy to control the fecal incontinence of patient 12. In the example shown in FIG. 1, the distal end of lead 36 is inserted into sacral foramen 30 of sacrum 28. Since second sacral nerve 32 may be known to innervate portions of intestines 23 such as rectum 24, electrodes 38 may be implanted adjacent to second sacral nerve 32 to evaluate the efficacy of therapy delivered to this site. In this manner, the second sacral nerve 32 may be associated with the anatomical regions of intestines 23 and rectum 24. A nerve or nerves which innervate or otherwise carry impulses to or away from an anatomical region may be referred to as a nerve associated with the anatomical region. In other examples, stimulation of second sacral nerve 32 may be performed using electrodes external of the pelvic floor either subcutaneously implanted or placed on the external surface of the skin. However, these other locations may not be sufficiently precise to evaluate stimulation therapy. In some examples, stimulation may be delivered to second sacral nerve 32 and additional nerves adjacent to the sacral nerve. For example, stimulation may be delivered to both S2 and S3 nerves.

In examples directed to treating fecal incontinence, stimulator 34 may be configured to deliver electrical stimulation to second sacral nerve 32 according to a selected set of stimulation therapy parameter values. This set of therapy parameter values may at least partially define the electrical stimulation and include parameter values for one or more therapy parameters such as current amplitude, voltage amplitude, pulse width, pulse frequency, waveform shape (in examples that include continuous waveform delivery) and electrode combinations. The set of therapy parameter values may be selected according to clinician experience, patient condition, or any other circumstances. Fecal incontinence may also be treated by stimulating one or more other nerves in addition or alternative to second sacral nerve 32. For example, stimulation may be directed to one or more of a pelvic floor nerve, a pelvic floor muscle, the anal sphincter, or other pelvic floor targets. Pelvic floor nerves include peripheral nerves such as sacral nerves, pudendal nerves and associated branches, and dorsal genital nerves.

In the example shown in FIG. 2, lead 36 is cylindrical. Electrodes 38 leads 36 may be ring electrodes, segmented electrodes, or partial ring electrodes. Segmented and partial ring electrodes each extend along an arc less than 360 degrees (e.g., 90-120 degrees) around the outer perimeter of lead 36. In some examples, lead 36 may have a complex electrode geometry. An example of a complex electrode array geometry may include an array of electrodes located at different axial positions along the length of a lead in addition to electrodes located at different angular positions about the periphery, e.g., circumference, of the lead 36. In examples, lead 36 may be, at least in part, paddle-shaped (i.e., a "paddle" lead), e.g., where an array of electrode pads are provided in a two-dimensional array on a surface of the paddle lead. In some examples, one or more of electrodes 38 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize discomfort to patient 12. An electrical field represents the areas of a patient anatomical region that will be covered by an electrical field during delivery of stimulation therapy to tissue within patient 12. The electrical field may define the volume of tissue that is affected when the electrodes 38 are activated. An activation field represents the neurons that will be activated by the electrical field in the neural tissue proximate to the activated electrodes.

Additionally, or alternatively, system 22 may be configured to control delivery of electrical stimulation and sense eCMAP biomarkers to screen for effective therapy to treat a bladder related condition of patient 12. In some examples directed to treatment of bladder related conditions, lead 36 may directed through sacral foramen 76 in order for stimulator 34 to deliver electrical stimulation to third sacral nerve 78 via one or more electrodes 38 of lead 36. Third sacral nerve 78 may innervate anatomical regions associated with urinary incontinence such as the muscular wall of bladder 40 and urinary sphincter 42. Additional or alternative nerves may also be targeted by one or more of electrodes 38.

As discussed above with respect to fecal incontinence, stimulation may be applied to third sacral nerve 78 while a far-field signal is monitored for an eCMAP biomarker via electrodes 38. During programming, stimulation intensity may be incrementally raised until an eCMAP biomarker appears in the far-field signal. Therapeutic stimulation may be programmed to be delivered at a percentage of the stimulation intensity which resulted in the eCMAP biomarker.

In some examples, system 22 may include an electrode patch 44, or other electrode located in an area near the target of applied stimulation. For example, electrode patch may be located in an area near the rectum when system 22 is used to treat fecal incontinence. Electrode patch 44 may collect a near-field signal including an eCMAP biomarker.

Figure 3:
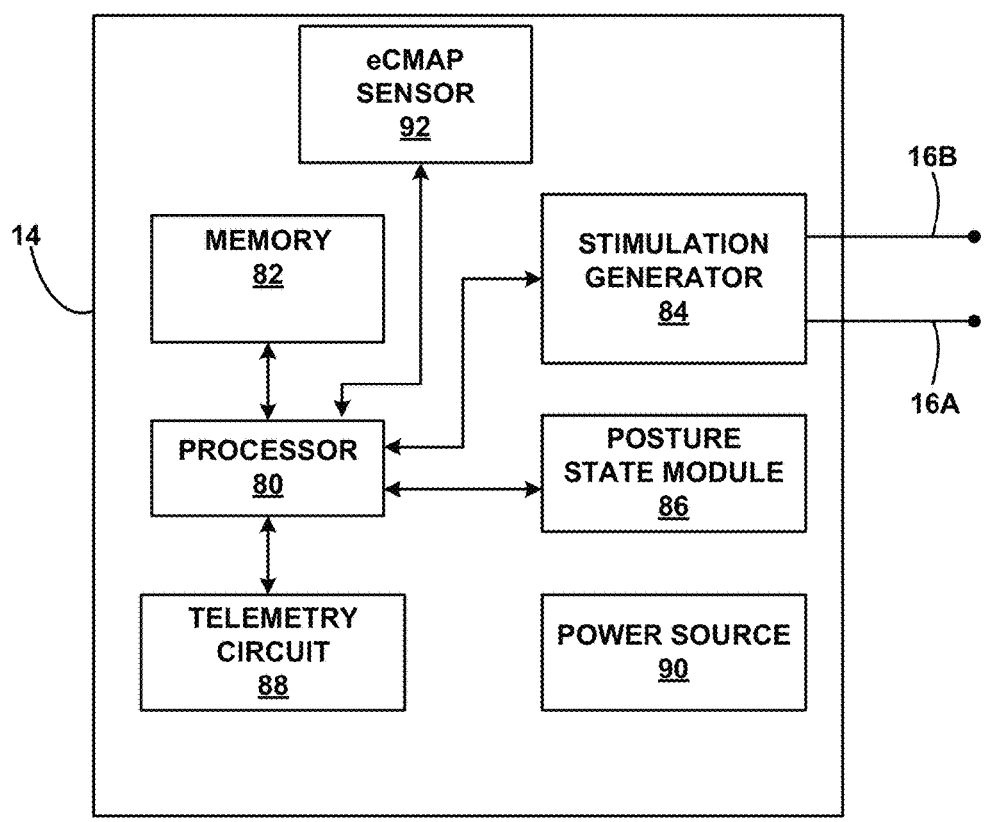
FIG. 3 is a functional block diagram illustrating example components of an IMD, such as the IMD in FIG. 1.

FIG. 3 is a functional block diagram illustrating various components of an IMD 14. In the example of FIG. 3, IMD 14 includes a processor 80, memory 82, stimulation generator 84, posture state module 86, telemetry circuit 88, power source 90, and eCMAP sensor 92. The stimulation generator 84 forms a therapy delivery module. Memory 82 may store instructions for execution by processor 80, stimulation therapy data, eCMAP biomarkers, posture state information, posture state indications, and any other information regarding therapy or patient 12. Therapy information may be recorded for long-term storage and retrieval by a user, and the therapy information may include any data created by or stored in IMD 14. Memory 82 may include separate memories for storing instructions including instructions for eCMAP analysis, posture state information, therapy adjustment information, prior detected eCMAP biomarkers, program histories, and any other pertinent data or instructions.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current sources and sinks to drive more than one electrode combination at one time. For example, each electrode may have its own current source and current sink, which can be selectively activated so that the electrode can source or sink controlled amounts of current. An electrode configuration, e.g., electrode combination and associated electrode polarities, may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy.

In other examples, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

According to examples described herein, such stimulation parameters may be adjusted to modify stimulation therapy delivered by IMD 14 based on the detected eCMAP biomarker of patient 12. In some examples, processor 80 may detect an eCMAP biomarker of patient 12 via eCMAP sensor 92 that indicates that a modification of the stimulation therapy is appropriate, e.g., according to instructions stored in memory 82. Processor 80 may access instructions for modifying the stimulation therapy based on the detected eCMAP biomarker, e.g., by changing from the current stimulation program to a program which results in a desired eCMAP biomarker.

According to other examples described herein, such stimulation parameters may be adjusted to modify stimulation therapy delivered by IMD 14 based on a combination of the detected eCMAP biomarker and a detected posture state. In some examples, processor 80 may detect an eCMAP biomarker of patient 12 via eCMAP sensor 92 as well as a posture state of patient 12 via posture state module 86. If a change in eCMAP biomarker has been detected, a detected posture state may be used to help processor 80 determine the appropriate stimulation program in order to achieve a desired eCMAP biomarker. For example, memory 82 may include a stimulation program associated with the detected posture state which resulted in the desired eCMAP biomarker in the past.

An exemplary range of electrical stimulation parameters likely to be effective in treating chronic pain, e.g., when applied to spinal cord 18, are listed below. However, other parameter values are contemplated. While stimulation pulses are described, stimulation signals may be of any of a variety of forms such as sine waves or the like.

Pulse Rate: between approximately 0.5 Hz and 10 kHz, more preferably between approximately 5 Hz and 250 Hz, and still more preferably between approximately 30 Hz and 130 Hz.

Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between 0.1 milliamps (mA) and 50 mA.

Pulse Width: between about 10 microseconds and 5000 microseconds, more preferably between approximately 100 microseconds and 1000 microseconds, and still more preferably between approximately 180 microseconds and 450 microseconds.

In other applications, different ranges of parameter values may be used. For deep brain stimulation (DBS), as one example, alleviation or reduction of symptoms associated with Parkinson's disease, essential tremor, epilepsy or other disorders may make use of stimulation having a pulse rate in the range of approximately 0.5 to 1200 Hz, more preferably 5 to 250 Hz, and still more preferably 30 to 185 Hz, and a pulse width in the range of approximately 10 microseconds and 5000 microseconds, more preferably between approximately 60 microseconds and 1000 microseconds, still more preferably between approximately 60 microseconds and 450 microseconds, and even more preferably between approximately 60 microseconds and 150 microseconds. Amplitude ranges such as those described above with reference to SCS, or other amplitude ranges, may be used for different DBS applications. Parameter values other than those described above are contemplated.

Processor 80 accesses stimulation parameters in memory 82, e.g., as programs and groups of programs. Upon selection of a particular program group, processor 80 may control stimulation generator 84 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

In some examples, IMD 14 includes a posture state module 86 which allows IMD 14 to sense or detect the current patient posture state, e.g., posture, activity or any other static position or motion of patient 12. In the example of FIG. 2, posture state module 86 may include one or more accelerometers, such as three-axis accelerometers, capable of detecting static orientation or vectors in three-dimensions. The three-axis accelerometer may be a micro-electro-mechanical accelerometer. In other examples, posture state module 86 may alternatively or additionally include one or more gyroscopes, pressure transducers or other sensors to sense the current posture state occupied by patient 12. Posture state information generated by posture state module 86 and processor 80 may correspond to an activity and/or posture undertaken by patient 12 or a gross level of physical activity, e.g., activity counts based on footfalls or the like.

Posture state information from posture state module 86 may be stored in memory 82 for later review by a clinician, used to adjust therapy, present a posture state indication to patient 12 and/or clinician, e.g., via user interface display of external programmer 20, or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture state. IMD 14 may also store which group or program was being used to deliver therapy when patient 12 was in the sensed posture state. Further, processor 80 may also adjust therapy for a new posture state when posture state module 86 indicates that patient 12 has in fact changed postures. In some examples, the change in posture may trigger sensing of eCMAP. Based on the sensed eCMAP from eCMAP sensor 92, processor 80 may determine an appropriate adjustment to one or more current stimulation therapy parameters in order to achieve a desired eCMAP biomarker. In some examples, a current eCMAP biomarker may be compared to an eCMAP template corresponding to efficacious therapy.

Therefore, IMD 14 may be configured to provide eCMAP responsive stimulation therapy to patient 12. Stimulation adjustments in response to changes in eCMAP biomarker or to patient state may be automatic or semi-automatic (subject to patient approval). In many cases, fully automatic adjustments may be desirable so that IMD 14 may react more quickly to changes in patient state, or changes in therapy efficacy that may be unrelated to a change in patient state. In some examples, eCMAP sensing and analysis may be used to refine stimulation therapy programs selected based on sensed posture.

Memory 82 may include definitions for each posture state of patient 12. In one example, the definitions of each posture state may be illustrated as a cone in three-dimensional space. Whenever the posture state parameter value, e.g., a vector, from the three-axis accelerometer of posture state module 86 resides within a predefined cone or volume, processor 80 indicates that patient 12 is in the posture state of the cone or volume. In other examples, a posture state parameter value from the 3-axis accelerometer may be compared to values in a look-up table or equation to determine the posture state in which patient 12 currently resides. Examples techniques for detecting a patient posture state include examples described in U.S. Pat. No. 8,708,934, titled "REORIENTATION OF PATIENT POSTURE STATES FOR POSTURE-RESPONSIVE THERAPY," filed Apr. 30, 2009 and issued Apr. 29, 2014, the entire content of which is incorporated by reference herein.

Adjustments to one or more stimulation parameters responsive to changes in sensed eCMAP may allow IMD 14 to implement a certain level of automation in therapy adjustments. In particular, IMD 14 may continuously, or on a periodic basis, adjust stimulation therapy parameters in order to maintain an eCMAP biomarker that corresponds to efficacious treatment. Automatically adjusting stimulation may free patient 12 from the constant task of manually adjusting therapy each time patient 12 changes posture. Automatically adjusting stimulation based on sensed eCMAP may also correct for natural drift of leads 16 irrespective of posture state. For example, by detecting eCMAP biomarkers over time, processor 80 may determine that the location of the nerves being stimulated has changed over time. Such manual adjustment of stimulation parameters can be tedious, requiring patient 12 to, for example, depress one or more keys of patient programmer 20 multiple times during the patient posture state to maintain adequate symptom control. In some embodiments, patient 12 may eventually be able to enjoy eCMAP responsive stimulation therapy, which adjusts therapy according to changing conditions without the need to continue making changes for different patient states via patient programmer 20. Instead, patient 12 may transition immediately or over time to fully automatic adjustments based on eCMAP biomarker alone or in combination with detected patient states such as posture.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple activity sensors placed at various locations on or within the body of patient 12.

In some examples, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some embodiments, to confirm or reject changes in sensed posture state that may result from vibration, patient travel (e.g., in an aircraft, car or train), or some other false positive of posture state. In some examples, the one or more physiological parameters may be used to determine a patient state other than posture. In addition, eCMAP sensing and analysis may be used to confirm a change in the relationship between the stimulation source and stimulation target within patient 12.

In addition, IMD 14 may store patient 12 input regarding perceived physiological conditions (e.g., symptoms) not detectable by any implemented sensors. For example, patient 12 may provide input to patient programmer 30 that indicates where the patient perceives any symptoms and characteristics of that particular type of symptom. Processor 80 may associate this physiological condition information with the currently detected posture state, the stimulation parameters, and/or a time stamp to provide a complete therapy picture to the patient or clinician at a later time. Such information may be stored in memory 82 of IMD 14, the memory of programmer 20, and/or the memory of other device.

Wireless telemetry in IMD 14 with external programmer 20, e.g., a patient programmer or a clinician programmer, or another device may be accomplished by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. Further, telemetry circuit 88 may transmit information, e.g., eCMAP biomarker data, in real-time when communicating to an external device. For eCMAP data sent in real-time, telemetry circuit 88 may send the most recently detected eCMAP biomarker or a rolling average eCMAP biomarker at a relative high frequency, e.g., at or near the fastest rate supported by the telemetry circuit. As described above, in some examples, raw signal information from eCMAP sensor 92 may be transmitted to an external device for analysis by the external device to determine the eCMAP biomarker of patient 12. To support RF communication, telemetry circuit 88 may include appropriate electronic components, such as amplifiers, filters, mixers, encoders, decoders, and the like.

When an eCMAP parameter value indicates that the stimulation program administered to patient 12 has changed efficacy, processor 80 may communicate with patient programmer 20 via telemetry circuitry 88 to indicate the newly detected change in eCMAP biomarker, i.e., a new eCMAP biomarker that indicates the current efficacy of the stimulation being provided to patient 12. Alternatively, processor 80 may periodically or non-periodically send eCMAP biomarker information to patient programmer 20 either unilaterally or in response to a request from patient programmer 20. For example, patient programmer 20 may request the most current eCMAP biomarker, and transmit changes in stimulation parameter values back to IMD 14 based on analysis of the most current eCMAP biomarker.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some embodiments, power requirements may be small enough to allow IMD 14 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 14 when needed or desired.

ECMAP sensor 92 detects far-field eCMAP signals. In some examples, eCMAP sensor 92 may be located on lead 16, and may include for, example, one or more of the electrodes in leads 16 in combination with suitable amplification, filtering and/or signal processing circuitry. In some examples, eCMAP sensor 92 may include additional electrode on the housing of IMD 14. In some examples eCMAP sensor 92 may be carried by an additional sensor lead positioned somewhere within patient 12, provided as an independent implantable sensor, or even worn on patient 12. For example, one or more microsensors may be implanted within patient 12 to communicate sensed eCMAP biomarkers wirelessly to IMD 14. In this manner the eCMAP sensed responses may be obtained independent of the location of the electrodes delivering electrical stimulation therapy.

Figure 4:
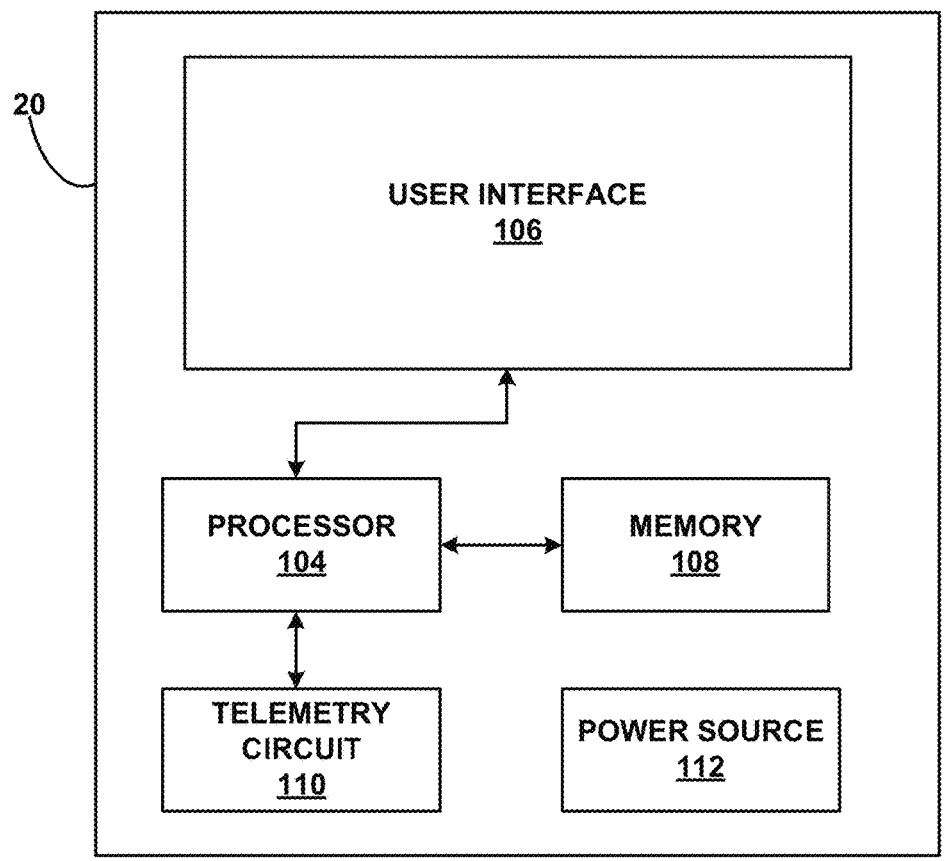
FIG. 4 is a functional block diagram illustrating example components of an external programmer for an IMD, such as the IMD in FIG. 1.

FIG. 4 is a functional block diagram illustrating various components of an external programmer 20 for IMD 14. As shown in FIG. 4, external programmer 20 is an external device that includes processor 104, memory 108, telemetry circuit 110, user interface 106, and power source 112. External programmer 20 may be embodied as a patient programmer or a clinician programmer. A clinician or patient 12 interacts with user interface 106 in order to manually change the stimulation parameters of a program, change programs within a group, turn eCMAP responsive stimulation ON or OFF, view therapy information, view patient state information, view a posture state indication, or otherwise communicate with IMD 14.

User interface 106 may include a screen and one or more input buttons, as in the example of a patient programmer, that allow external programmer 20 to receive input from a user. Alternatively, user interface 106 may additionally or only utilize a touch screen display, as in the example of a clinician programmer. As described herein, user interface may be embodied as example user interfaces 200, 270, or 290. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Input buttons for user interface 106 may include a touch pad, increase and decrease buttons, emergency shut off button, and other buttons to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

Telemetry circuit 110 allows the transfer of data to and from IMD 14, or IMD 26. Telemetry circuit 110 may communicate automatically with IMD 14 in real-time, at a scheduled time, or when the telemetry circuit detects the proximity of the stimulator. User interface 106 may then update displayed information accordingly. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. Alternatively, a recharging device may be capable of communication with IMD 14. Then, the recharging device may be able to transfer programming information, data, or any other information described herein to IMD 14. In this manner, the recharging device may be able to act as an intermediary communication device between external programmer 20 and IMD 14. In other cases, the programmer may be integrated with a recharging functionality in the combined programming/recharging device. The techniques described herein may be communicated between IMD 14 via any type of external device capable of communication with IMD 14.

Figure 5:
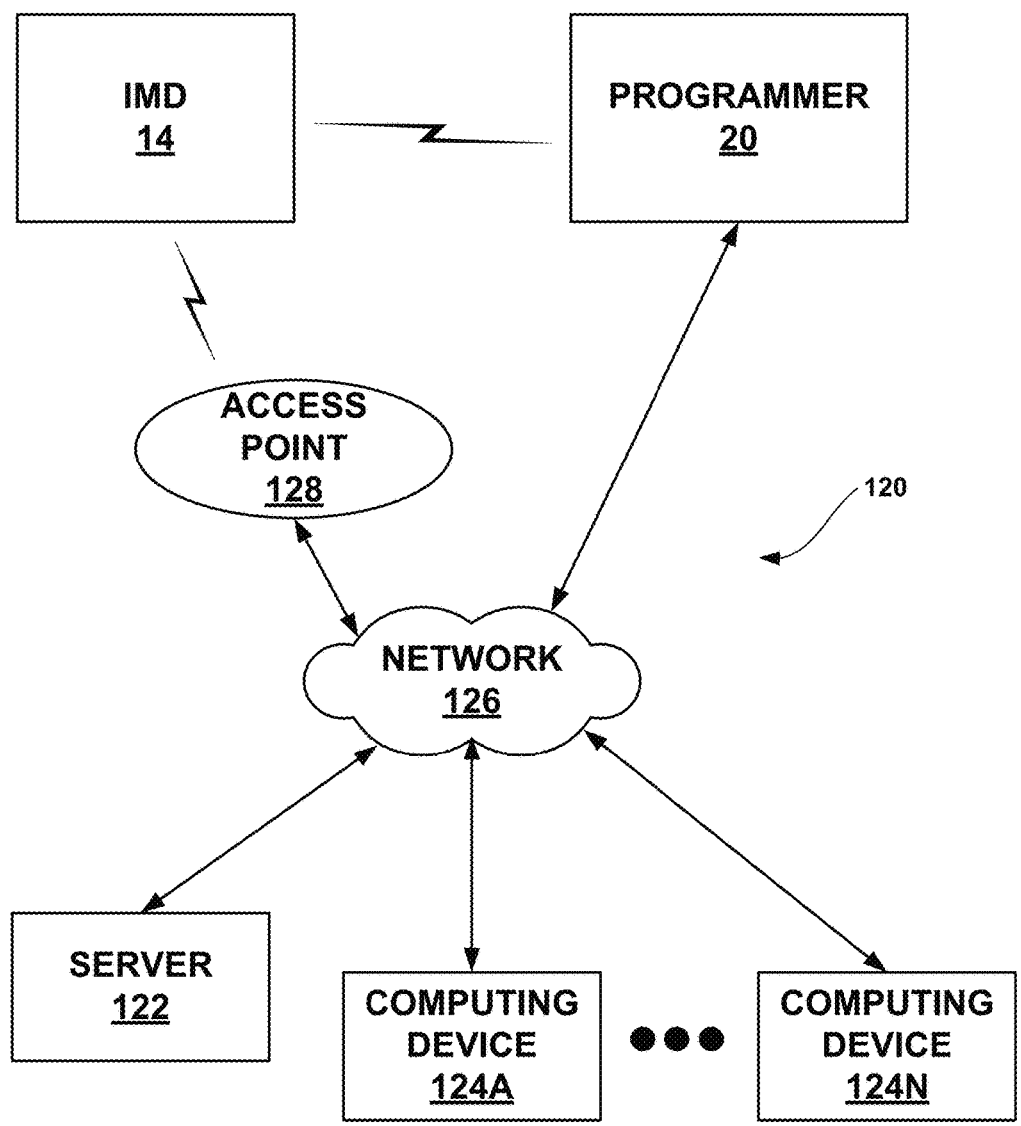
FIG. 5 is a block diagram illustrating an example system that includes an external device, such as a server, and one or more computing devices, that are coupled to IMD and external programmer shown in FIG. 1 via a network.

FIG. 5 is a block diagram illustrating an example system 120 that includes an external device, such as a server 122, and one or more computing devices 124A-124N, that are coupled to IMD 14 and external programmer 20 shown in FIG. 1 via a network 126. In this example, IMD 14 may use its telemetry circuit 88 to communicate with external programmer 20 via a first wireless connection, and to communication with an access point 128 via a second wireless connection.

In the example of FIG. 5, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, digital signal processors (DSPs), application specific integrated circuits (ASICs), field programmable gate arrays (FPGAs), programmable logic circuitry, or the like, that may perform various functions and operations, such as those described in this disclosure Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of data. For example, IMD 14 may collect sensed eCMAP biomarkers and posture state information during therapy that indicate how patient 12 moves throughout each day, and movement of leads 16 with respect to the stimulation target. In some cases, IMD 14 may directly analyze the collected data to evaluate efficacy of adjustments to stimulation therapy based sensed patient posture. In other cases, however, IMD 14 may send stored data relating to posture state information and sensed eCMAP biomarker to external programmer 20 and/or server 122, either wirelessly or via access point 128 and network 126, for remote processing and analysis.

For example, IMD 14 may sense, process, trend and evaluate the sensed eCMAP response, posture state information, and other therapy information. This communication may occur in real time, and network 126 may allow a remote clinician to review the current patient posture state by receiving a presentation of a posture state indication along with other therapy information on a remote display, e.g., computing device 124A. Alternatively, processing, trending and evaluation functions may be distributed to other devices such as external programmer 20 or server 122, which are coupled to network 126. In addition, posture state information and other therapy information may be archived by any of such devices, e.g., for later retrieval and analysis by a clinician. For example, the archived therapy information may be presented to a user via user interface 106 (FIG. 3).

In some cases, IMD 14, external programmer 20 or server 122 may process posture state information, eCMAP biomarker, or raw data and/or therapy information into a displayable eCMAP biomarker report, which may be displayed via external programmer 20 or one of computing devices 124A-124N. The eCMAP report may contain trend data for evaluation by a clinician, e.g., by visual inspection of graphic data. In some cases, the eCMAP report may include the number of activities patient 12 conducted, a percentage of time patient 12 was in each posture state, how magnitude in change to the eCMAP biomarker for a particular change in posture, what group or program was being used to deliver therapy during each activity, the number of manual adjustments to therapy provided in addition to eCMAP responsive adjustments, or any other information relevant to patient 12 therapy, based on analysis and evaluation performed automatically by IMD 14, external programmer 20 or server 122. A clinician or other trained professional may review the historical therapy information including the stimulation parameters, physiological conditions, and changes in eCMAP in response to stimulation to possibly identify any problems or issues with the therapy that should be addressed.

In addition, network 126 may be configured to facilitate real-time communication between IMD 14 and computing device 124A for programming based on a currently sensed eCMAP biomarker. Although there may be some slight delay in the transfer of information, this may still be considered real-time programming utilizing any user interface such as user interfaces 200, 270, or 290. The clinician may be able to remotely visit with patient 12, review stored therapy information, and make any programming changes in real-time using system 120.

In some cases, server 122 may be configured to provide a secure storage site for archival of eCMAP biomarker and patient state information that has been collected from IMD 14 and/or external programmer 20. Network 126 may comprise a local area network, wide area network, or global network, such as the Internet. In other cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve eCMAP biomarkers, posture state information and related data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 20, or communicate with patient 12. In an additional example, the clinician may utilize system 120 to monitor multiple patients and share data with other clinicians in an effort to coordinate rapid evolution of effective treatment of patients. Further, eCMAP biomarker detection may be used to provide notifications, such as providing notification via a wireless link to a care giver a lead has shifted substantially.

Furthermore, although the disclosure is described with respect to SCS therapy, such techniques may be applicable to IMDs that convey other therapies the relationship between lead 16 and the target stimulation location may change, such as, e.g., DBS, pelvic floor stimulation, gastric stimulation, occipital stimulation, functional electrical stimulation, and the like.

As described above, in some examples, an external device, such as, e.g., external programmer 20 may present therapy information to a user via a user interface. The therapy information presented to a user may relate to therapy delivered to a patient by IMD 14 or other medical device. The therapy information presented by the external device may include eCMAP biomarker, patient posture state information, physiological therapy information, and therapy parameter information.

The therapy parameter information and physiological therapy information may be associated with a particular eCMAP biomarker. In some examples, the information may also be associated with patient posture state information. The same eCMAP biomarker may be associated with more than one patient posture state. For example, the therapy parameter information presented to a user may include an indicator of one or more therapy parameters programmed for delivery for a particular eCMAP biomarker or particular patient posture state indicated to the user by the user interface. In some examples, the therapy parameter information may include an indicator of previous adjustments made by a user to one or more therapy parameters for therapy delivered to a patient in order to achieve a desired eCMAP biomarker associated with efficacious therapy. In the case of physiological condition information, physiological conditions associated with patient posture state information may include physiological symptoms experienced by the patient when in a particular posture state.

The user interface of an external device may be configured to receive feedback from a user (e.g., a patient or clinician) regarding physiological conditions information and/or the therapy parameter information associated with patient posture state information. In one example, the external device including the user interface for presenting therapy information may receive one or more therapy parameters for the therapy associated with a specific posture state of the patient. Such therapy parameter adjustments may be communicated to IMD 14 or other device for delivering therapy to patient 12 for the associated posture state. In another example, the external device including the user interface for presenting the therapy information may receive input regarding one or more physiological conditions indicated by a patient for a particular posture state. The therapy information presented to a user may be updated based on the input received from a user via the user interface.

Figure 6A:
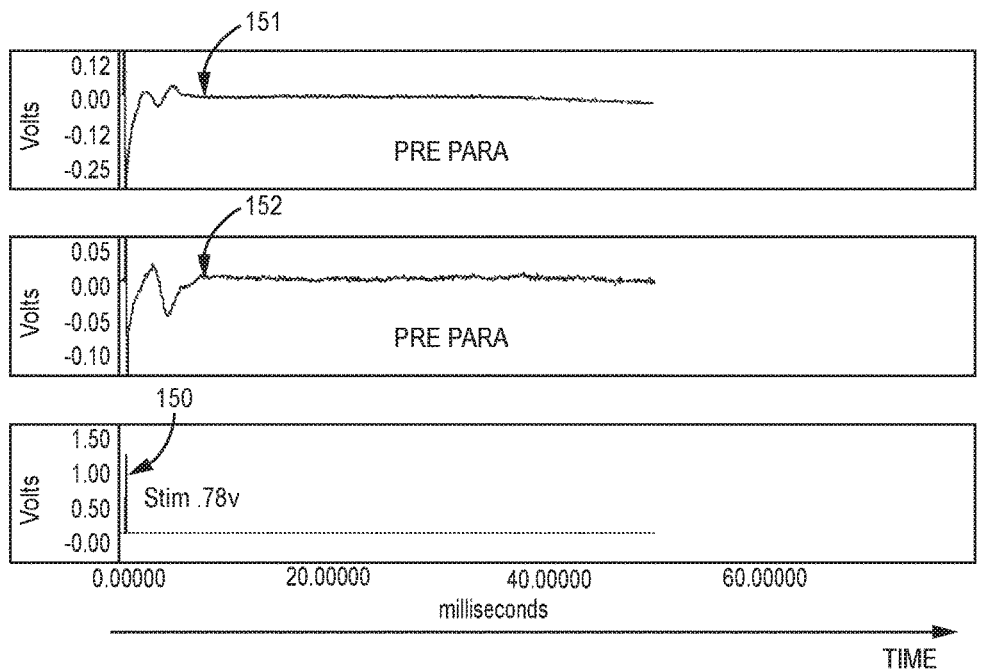
FIG. 6A is a graph showing an example eCMAP detected in response to the delivery of a stimulation pulse.

FIG. 6A is a graph showing an example eCMAP biomarker to the delivery of a stimulation pulse 150. The stimulation pulse 150 shows up in the signal detected by IMD 14. In addition the signal 152 detected by IMD 14 includes an eCMAP biomarker. The signal 152 includes a tri-phasic eCMAP biomarker. Signal 152 may be detected by an electrode on lead 16A or 16B, for example. Signal 151 is a signal collected by a needle electrode or other electrode near a target area intended to be activated by the applied stimulation. Signal 151 shows activation of the intended muscle. In FIG. 6A, the x-axis is in milliseconds and the y-axis in volts. In the example shown in FIG. 6A, the eCMAP biomarker in signal 152 beings approximately 5 milliseconds after the application of the stimulation pulse. The stimulation pulse 150 is approximately 0.73 V in amplitude. During programming of IMD 14, both signals 151 and 152 may be collected to help ensure that the eCMAP biomarker detected indicates the stimulation is activating the intended target area.

Figure 6B:
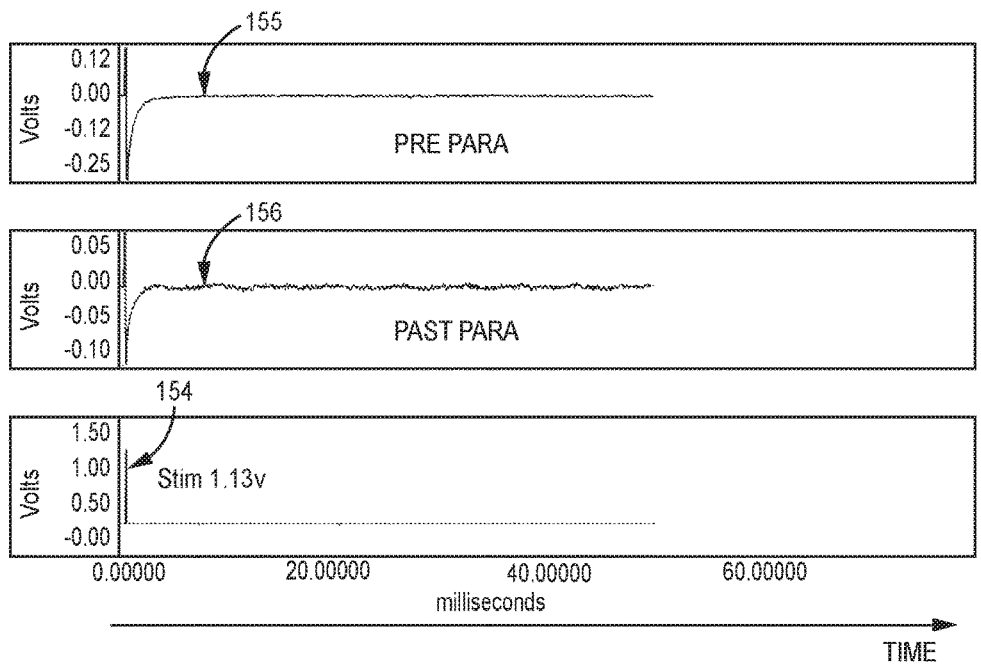
FIG. 6B is a graph showing the absence of an example in vivo, far-field eCMAP in response to stimulation after administration of a muscle paralytic.

FIG. 6B is a graph showing the absence of the in vivo far-field eCMAP in response to stimulation after administration of a muscle paralytic such as pancuronium bromide. Stimulation pulse 154 shows up in the signal detected by IMD 14. SAs shown in FIG. 6B, even with amplitude of stimulation pulse 154 increased to 1.13 V, signal 156 lacks an eCMAP biomarker. This indicates that the signal 156 detected by IMD is indeed a compound muscle action potential. Signal 155 is a signal detected by a needle electrode in or around the intended target area. Signal 155 also indicates that although the stimulation pulse is detected, no muscle activation has occurred. In some examples, not shown, confirmation of a far-field eCMAP may be obtained through muscle fatigue. For example, following stimulation at a frequency of approximately 3.5 kHz, the far-field eCMAP in response to stimulation may be absent as well.

Figure 7:
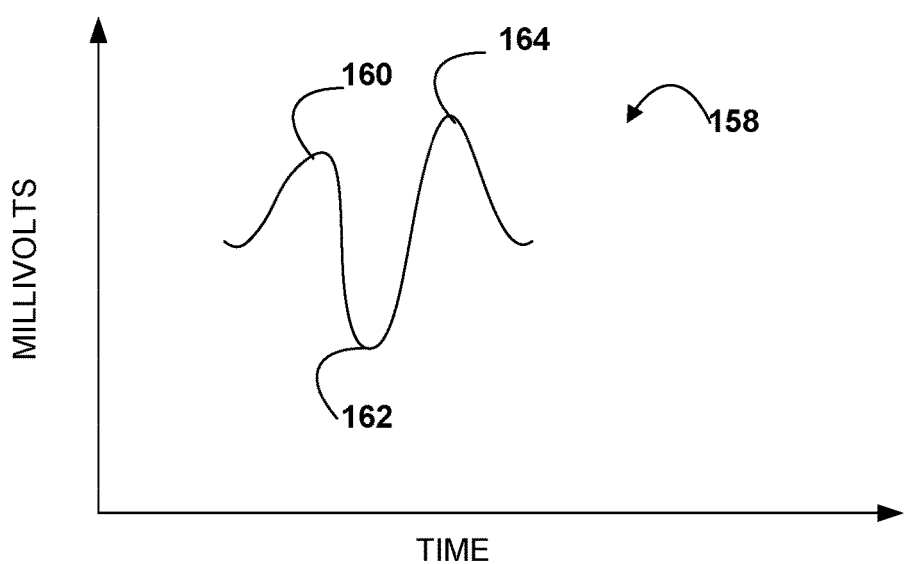
FIG. 7 is graphical representation of an example far-field eCMAP biomarker to stimulation detected by an IMD.

FIG. 7 is graphical representation of a far-field eCMAP biomarker to stimulation detected by IMD 14. In this example, the far-field eCMAP 158 is tri-phasic. The tri-phasic shape of eCMAP 158 is a result of bipolar sensing by IMD 14. The detected far-field eCMAP is a result of the summation of single muscle fiber action potentials from a large number of muscle fibers. The eCMAP magnitude and morphology depends on a number of factors, including the number of fibers activated, the temporal activation pattern of said fibers, and the filtering characteristics of the biopotential amplifier, among others. The far-field eCMAP is much less strongly influenced by the distance from the sensing electrode. Irrespective of the eCMAP biopotential amplifier characteristics, the amount of time between the application of the stimulation pulse and the detection of the eCMAP biomarker is a function of the latency of the neuromuscular structures described hereinabove.

The far-field eCMAP biomarker 158 includes a first positive peak 160, a second negative peak 162, and a third positive peak 164. However, the far-field eCMAP may assume any number of other morphologies including monophasic, biphasic, quadriphasic or an arbitrary combination thereof so long as the signal represents the sensed far-field eCMAP. The morphology of the eCMAP biomarker may be dependent, in part, upon the location of one or more sensors used to detect the eCMAP biomarker.

Figure 8:
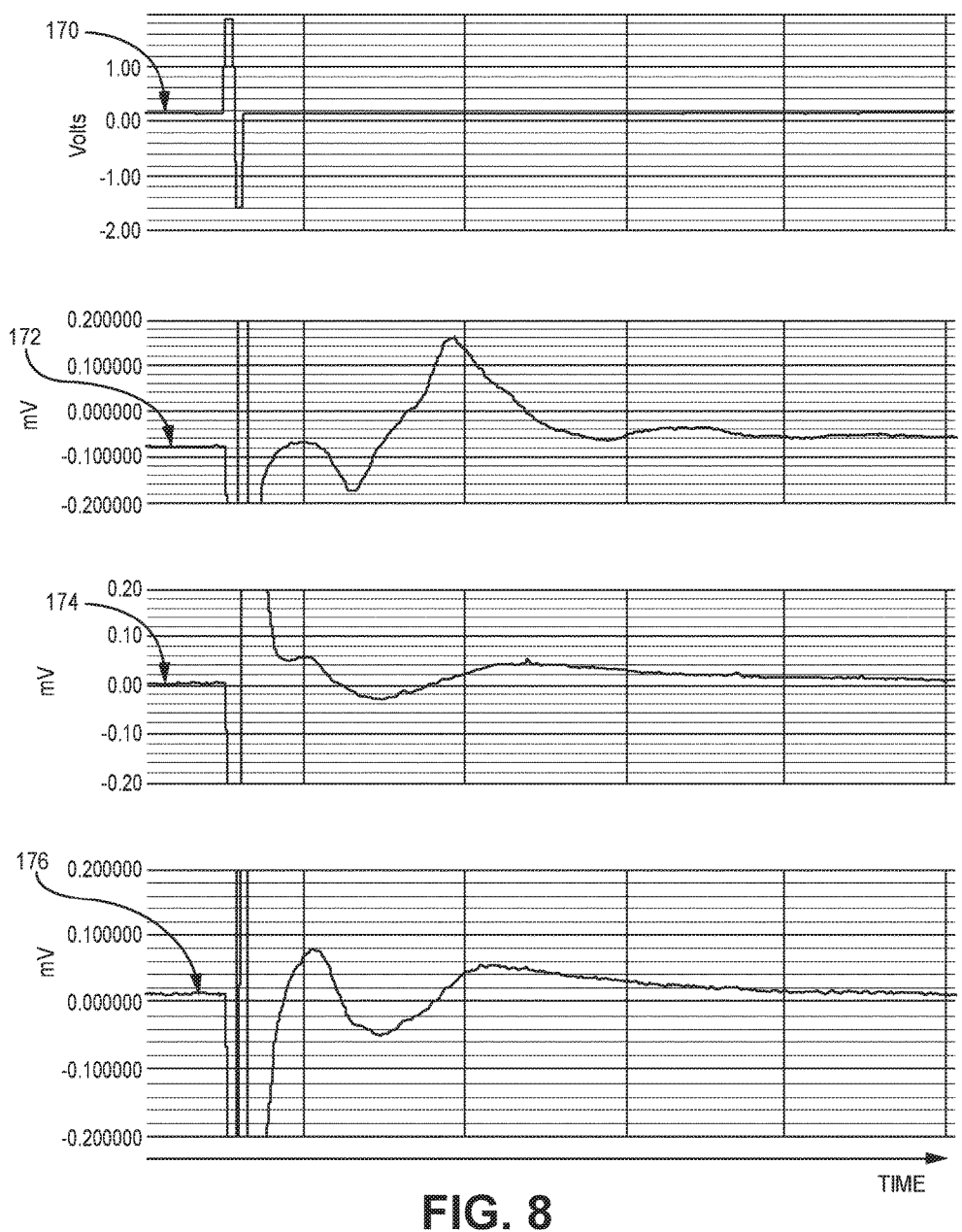
FIG. 8 is a graph showing a number of example EMG signals collected in response to the application of a stimulation pulse.

FIG. 8 is a graph showing a number of EMG signals collected in response to the application of stimulation pulse 170. Stimulation pulse may be provided to S2 or S3, for example. Signal 172 is an EMG signal detected by an electrode adjacent to the target area. Signal 172 includes a near-field eCMAP biomarker. For example, signal 172 may be collected by electrode patch 44. Signal 174 is an ipsilateral EMG signal. Signal 174 may be collected from an electrode on the same lead as the electrode delivering the stimulation pulse, for example. Signal 176 may be a contralateral EMG signal. Signal 176 may be collected from an electrode on a different lead from the electrode delivering the stimulation pulse, for example. Signals 174 and 176 include far-field eCMAP biomarkers.

Figure 9:
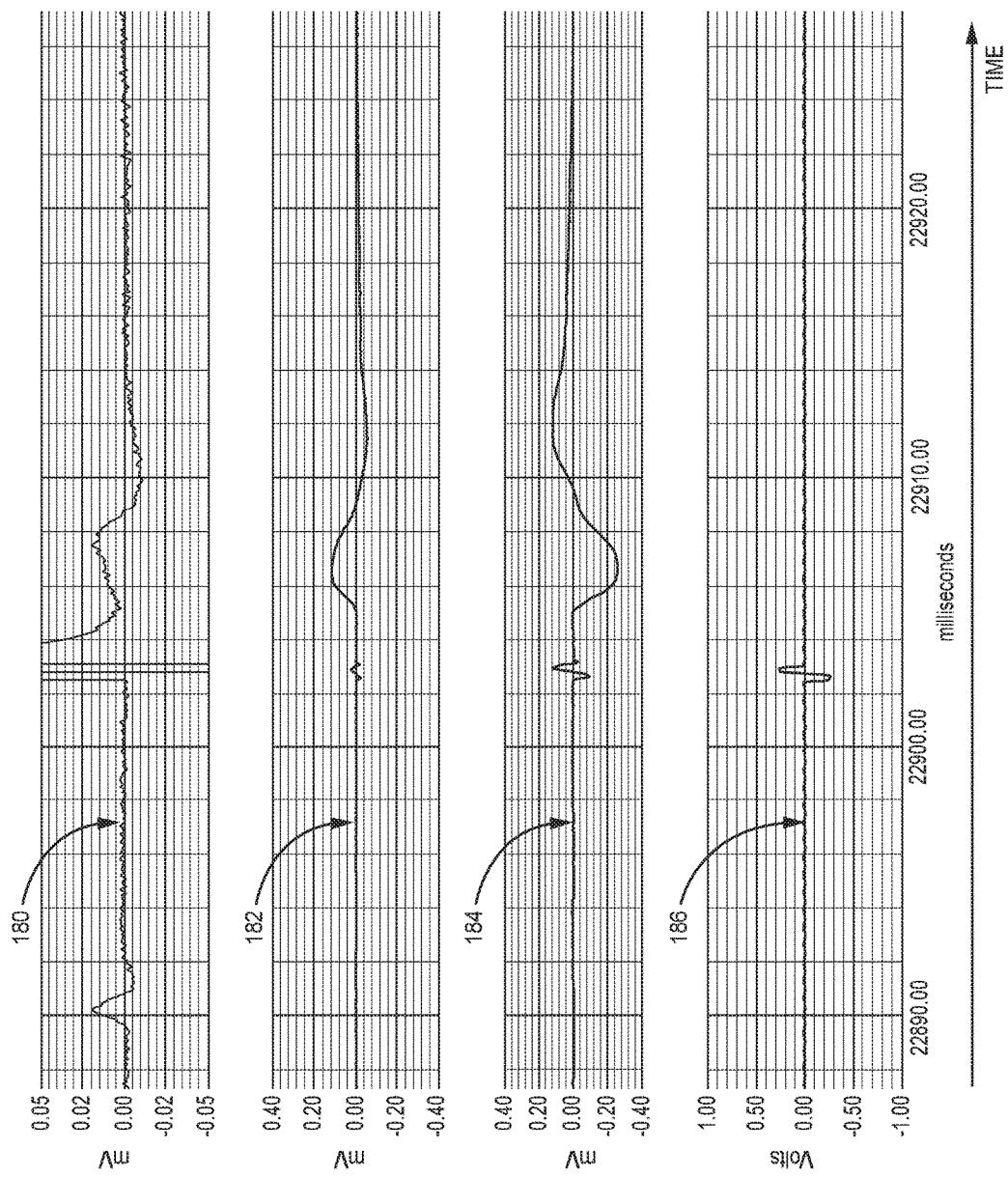
FIG. 9 is a graph showing examples of an eCMAP signal, a pair of EMG signals, and an applied stimulation signal used to elicit the eCMAP and EMG signals.

FIG. 9 is a graph showing example signals including an eCMAP signal 180, a first EMG signal 182, a second EMG signal 184, and stimulation signal 186 used in eliciting the eCMAP signal and EMG signals. The eCMAP signal 180, the first EMG signal 182, and the second EMG signal are detected in response to the stimulation signal 186 being applied using electrodes in the sacrum next to the sacral nerve of a sheep. The applied stimulation comprises stimulation pulses at approximately 0.27 volts with 210 microsecond pulse widths, the voltage scale at 0.50 volts per large division, the time scale at 10 milliseconds per large division.

Stimulation is applied at the ventral aspect aspect of the sheep's third sacral foramen, with a first electrode pair located in the left levator ani to provide the first EMG signal 182. The second EMG signal 184 is provided by electrodes embedded in the right levator ani. The amplitude axis of the EMC signals 182 and 184 are scaled at 200 microvolts per large division for both signals. The eCMAP signal 180 is provided by electrodes located in the S3 foramen, and thus may be located approximately two centimeters away from the levator ani where the stimulation signal 186 is applied. This is an example of a far-field eCMAP signal measurement. The amplitude axis of the eCMAP signal 180 is scaled to 20 microvolts per large division.

Figure 10:
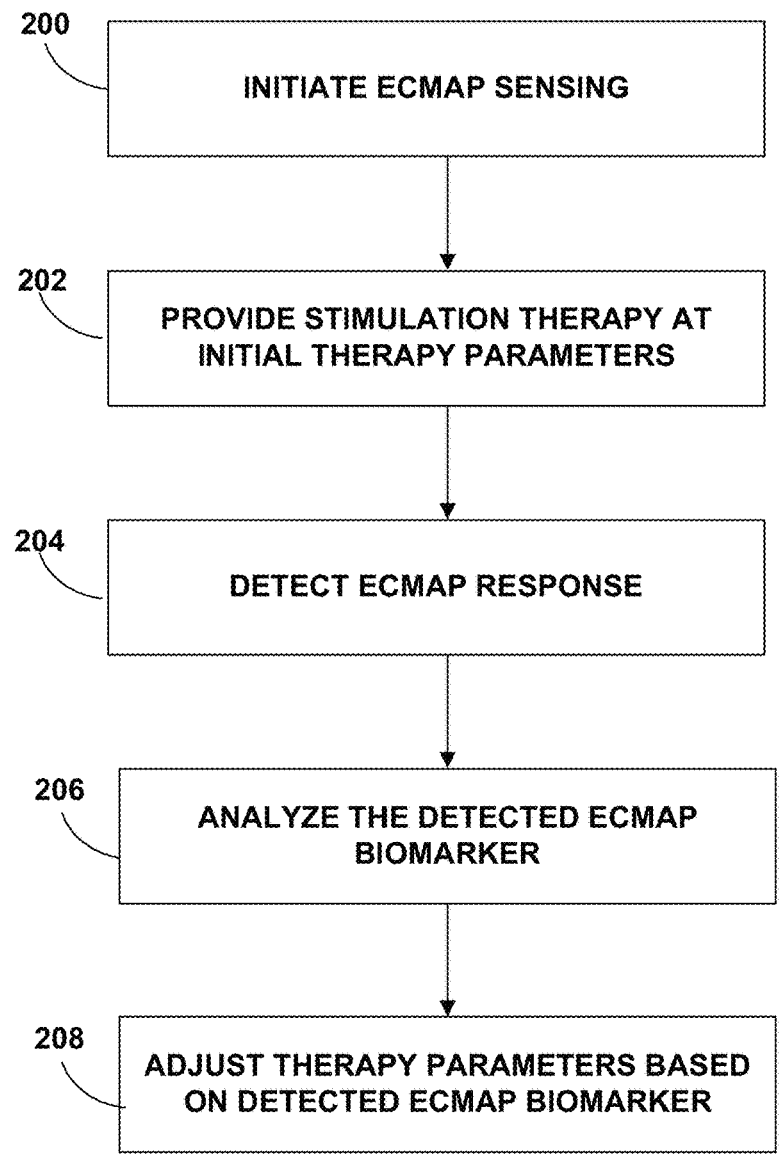
FIG. 10 is a flow diagram illustrating an example technique for adjusting electrical stimulation therapy parameters based on sensed eCMAP biomarkers to stimulation.

FIG. 10 is a flow diagram illustrating an example technique for adjusting stimulation therapy parameters based on sensed eCMAP biomarkers to stimulation. Although discussed with respect to IMD 14 of FIG. 1, the technique of FIG. 10 may be implemented, at least in part, by system 22 of FIG. 2. IMD 14 initiates eCMAP sensing (200) using eCMAP sensor 92. In some examples, eCMAP sensing may be initiated based on one or more different triggering events. For example, eCMAP sensing may be initiated based on an indication of a change in posture from posture module 86. In some examples, eCMAP sensing may be initiated based on user input. For example, a patient may indicate a change in efficacy of the current stimulation program. In other examples, eCMAP sensing may be initiated by processor 80 on a periodic basis. For example, processor 80 may turn on eCMAP sensor 92, every few seconds, minutes, hours or on a daily basis. Once eCMAP sensor 92 is turned on, processor 80 directs stimulation generator 84 to provide stimulation therapy at initial therapy parameters (202). The initial therapy parameters may be defined by a stimulation therapy program currently being used by IMD 14 to provide stimulation therapy. In some examples, the initial therapy parameters are an initial stimulation therapy program from which a user, such as a clinician begins programming IMD 14.

ECMAP sensor 92 detects the eCMAP biomarker (204) to stimulation provided according to the initial therapy parameters. The eCMAP sensor 92 may send a portion of the signal of a predetermined time length after the application of the stimulation signal to processor 80. Processor 80 then analyzes the detected eCMAP biomarker (206). In some examples, analysis of the eCMAP biomarker may include determining the magnitude of the eCMAP biomarker and the time between the stimulation pulse and the eCMAP response. In some examples, the eCMAP biomarker may be compared to a template of an eCMAP biomarker corresponding to desired stimulation results. For example, memory 82 may include a previously detected eCMAP biomarker stored when patient 12 previously indicated that therapy was efficacious. In some examples, various parameters of the eCMAP biomarker may be compared to parameters of a desired eCMAP biomarker. For example, processor 80 may compare the amplitude and time between delivery of stimulation and receipt of the eCMAP biomarker for the current eCMAP biomarker to those associated with efficacious therapy. Based on the analysis, processor 80 adjusts therapy parameters based on detected eCMAP biomarker (208). In some examples, stimulator generator 84 may then provide stimulation based on the adjusted therapy parameters.

Figure 11:
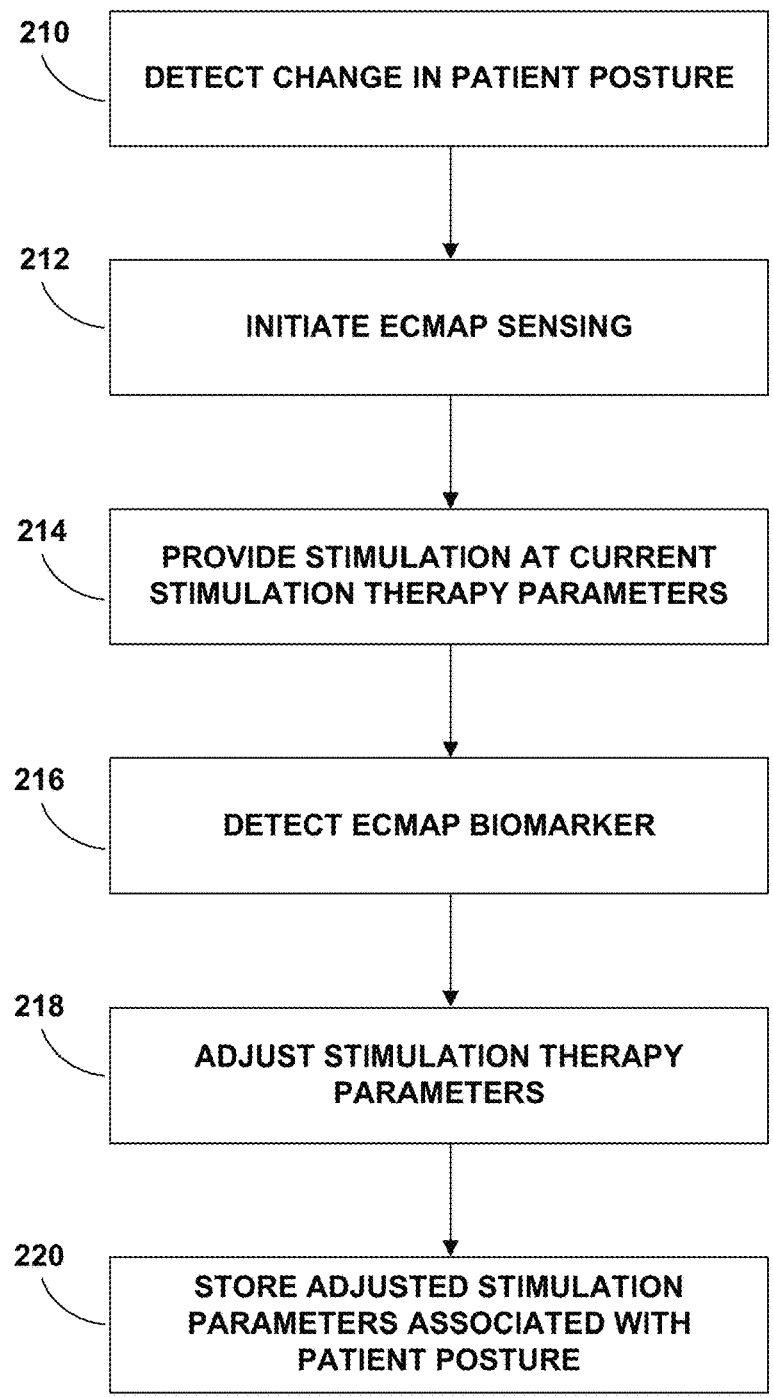
FIG. 11 is a flow diagram illustrating an example technique for adjusting electrical stimulation therapy parameters based on sensed eCMAP biomarkers to stimulation.

FIG. 11 is a flow diagram illustrating an example technique for adjusting stimulation therapy parameters based on sensed eCMAP biomarkers to stimulation. Although discussed with respect to system 10 of FIG. 1, the technique of FIG. 11 may be implemented, at least in part, by system 22 of FIG. 2. System 10 detects a change in patient posture (e.g., a change from a first posture state to a second posture state) (210). In some examples, IMD 14 detects the change in patient posture using posture state module 86. In some examples, a change in patient posture may be detected via patient input into external programmer 20. In response to detecting a change in patient posture, processor 80 initiates eCMAP sensing (212). A change in posture may result in a change in the eCMAP biomarker indicating a change in therapy efficacy. In some examples, initiating eCMAP sensing includes turning on eCMAP sensor 92.

Stimulation generator 84 provides stimulation at current stimulation therapy parameters (214). In some examples, current stimulation parameters are stimulation parameters associated with a therapy program being used to provide stimulation to patient 12 prior to the change in posture (e.g., a first posture state). In some examples, the current stimulation parameters are stimulation parameters associated with a therapy program used to provide stimulation to patient 12 after the change in posture (e.g., a second posture state). The therapy program used to provide stimulation to patient 12 after the change in posture may be different than the therapy program used to provide stimulation prior to the change in posture. In some examples, processor 80 automatically selects a therapy program from memory 82 upon detection of a change in patient posture (e.g., from a first posture state to a second posture state). In other words, in some examples, memory 82 (or another memory), may store different therapy programs that are associated with one or more respective posture states. In some examples, the current therapy parameters may be set by a clinician. For example, the technique of FIG. 8 may be implemented during initial programming or reprogramming of IMD 14.

ECMAP sensor 92 detects the eCMAP biomarker (216) to the stimulation provided to patient 12. In some examples, detection of the eCMAP biomarker includes monitoring a signal for a predetermined amount of time after the application of the stimulation pulse by stimulation generator 84. After detection processor 80 adjusts stimulation therapy parameters (218) based on the detected eCMAP biomarker. In some examples, the adjustment to stimulation parameters may be made based in part on a comparison of the detected eCMAP biomarker to an eCMAP biomarker saved in memory 82. The eCMAP biomarker saved in memory 82 may correspond to an eCMAP biomarker for the current position corresponding to previously effective stimulation parameters. In some examples, the eCMAP biomarker may be for the same set of stimulation parameters and in some examples, for a different set of stimulation parameters, then for the detected eCMAP biomarker.

In some examples, adjustment to the stimulation parameters (218) is an iterative process. For example, processor 80 may adjust stimulation parameters, apply new stimulation parameters, and detect an eCMAP biomarker until the eCMAP biomarker detected corresponds to a desired eCMAP biomarker. Once effective stimulation therapy parameters have been determined, processor 80 stores the adjusted stimulation parameters in memory 82 associated with the patient posture (220). In some examples, the next time patient 12 is detected to be in the posture state, stimulation generator may apply the stimulation parameters store in memory 82. Any necessary adjustments the next time the patient enters the posture state may be made based on a detected eCMAP biomarker for the stimulation parameters stored in the memory 82.

Figure 12:
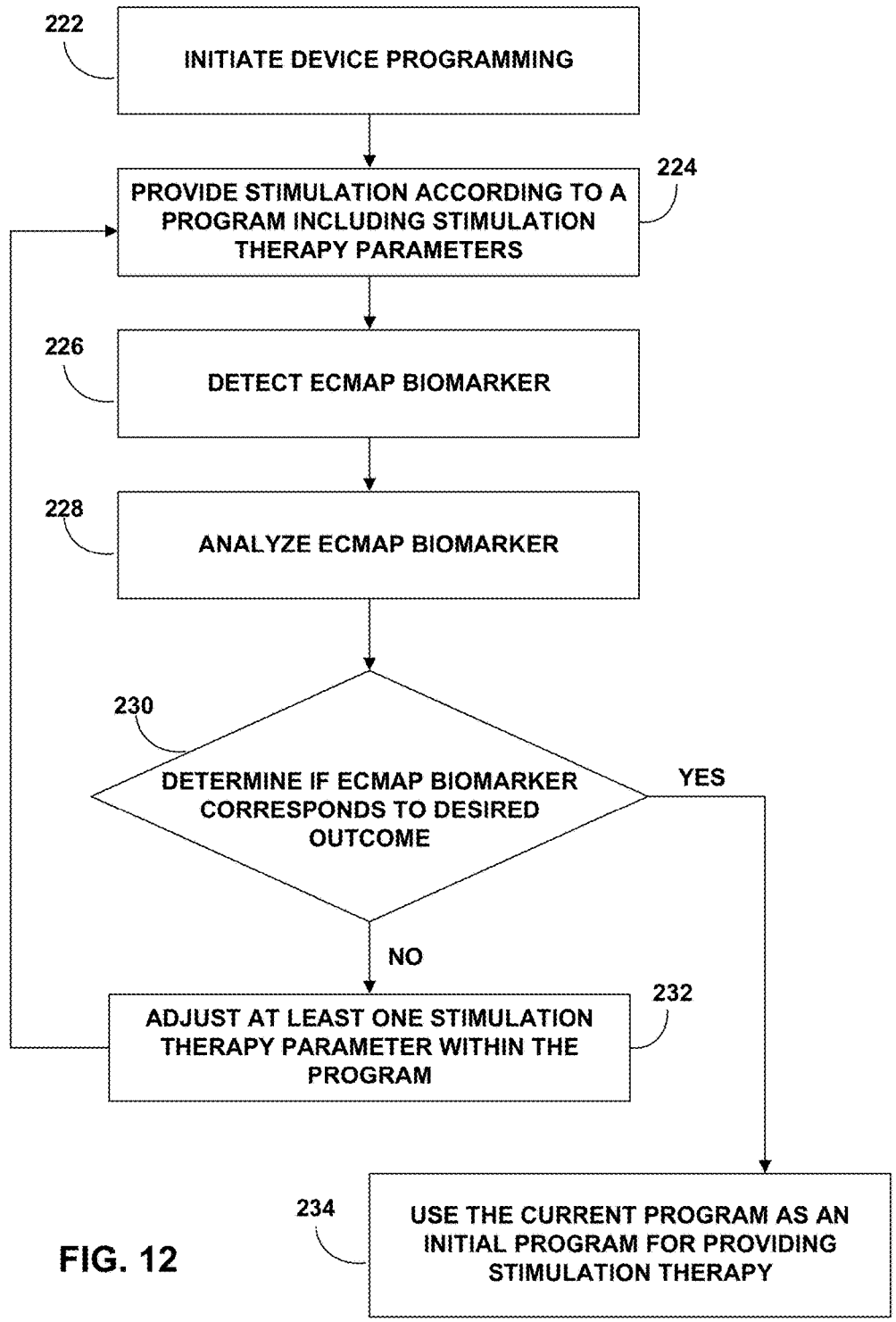
FIG. 12 is a flow diagram illustrating an example technique for adjusting electrical stimulation therapy parameters consistent with this disclosure.

FIG. 12 is a flow diagram illustrating an example technique consistent with the present disclosure. Although discussed with respect to system 10 of FIG. 1, the technique of FIG. 12 may be implemented, at least in part, by system 22 of FIG. 2. System 10 initiates device programming (222). In some examples, device programming may be initiated automatically by IMD 14. For example, device programming may occur at regular intervals, such as daily, weekly or monthly. In some examples, IMD 14 may automatically initiate programming in response to a detection by posture state module 86 that the posture of patient 12 has changed. In some examples, external programmer 20 may initiate device programming (222). For example, patient may provide input indicating that current therapy has lost effectiveness. In other examples, a clinician may use external programmer 20 to initiate device programming (222). For example, a clinician may do initial programming of IMD 14 while patient 12 is in the office, or follow-up programming during a follow-up visit by patient 12.

Once device programming has been initiated, IMD 14 provides stimulation according to a therapy program including a set of stimulation therapy parameters (224). In some examples, the therapy program may be the therapy program currently being used by IMD 14 to provide stimulation therapy to patient 12. In some examples, the therapy program may be an initial therapy program used to start device programming. The initial therapy program may include base values for electrode location, stimulation pulse width, stimulation frequency, and stimulation amplitude, for example. IMD 14 then detects an eCMAP biomarker (226) using eCMAP sensor 92. Detection of the eCMAP biomarker may include capturing a far-field signal for a predetermined amount of time after the application of the stimulation pulse. Processor 80 analyzes the detected eCMAP biomarker (228). Analysis may include, determining if an eCMAP biomarker is present in the signal, determining the time between the application of the stimulation pulse and the receipt of the eCMAP biomarker by eCMAP sensor 92, determining the amplitude of the eCMAP biomarker, or comparing the detected signal to a template of a desired eCMAP biomarker, for example. Based on the analysis, processor 80 determines if the eCMAP biomarker corresponds to a desired outcome (230). For example, if analysis indicates that effective therapy is being provided to the patient 12, then IMD 14 determines that the desired outcome has reached, and programming is ended. In some examples, processor 80 determines that the eCMAP biomarker indicates the stimulation therapy falls within a predetermined range of symptom relief, and side effects below a predetermined level. If the analysis of the eCMAP biomarker indicates that the desired outcome has been achieved, then IMD 14 uses the current therapy program as an initial therapy program for providing stimulation therapy (234).

In some examples, the initial therapy program may not be the first therapy program that has been used by IMD 14, but rather a therapy program used going forward until the next time device programming is initiated. If the eCMAP biomarker does not correspond to the desired outcome, then processor 80 adjusts at least one stimulation therapy parameter within the therapy program (232). For example, if the analysis indicates that the therapy program does not result in activation of the muscle action potential, then the total intensity of the stimulation therapy pulse may be increase. This may include increasing the amplitude of the stimulation pulse, the length of the stimulation pulse, or both. Stimulation generator 84 provides stimulation according to the updated therapy program (224). The process of providing stimulation (224), detecting an eCMAP biomarker (226), analyzing the eCMAP biomarker (228), and determining if the eCMAP biomarker corresponds to the desired outcome (230) is repeated until the eCMAP biomarker corresponds to the desired outcome.

Figure 13:
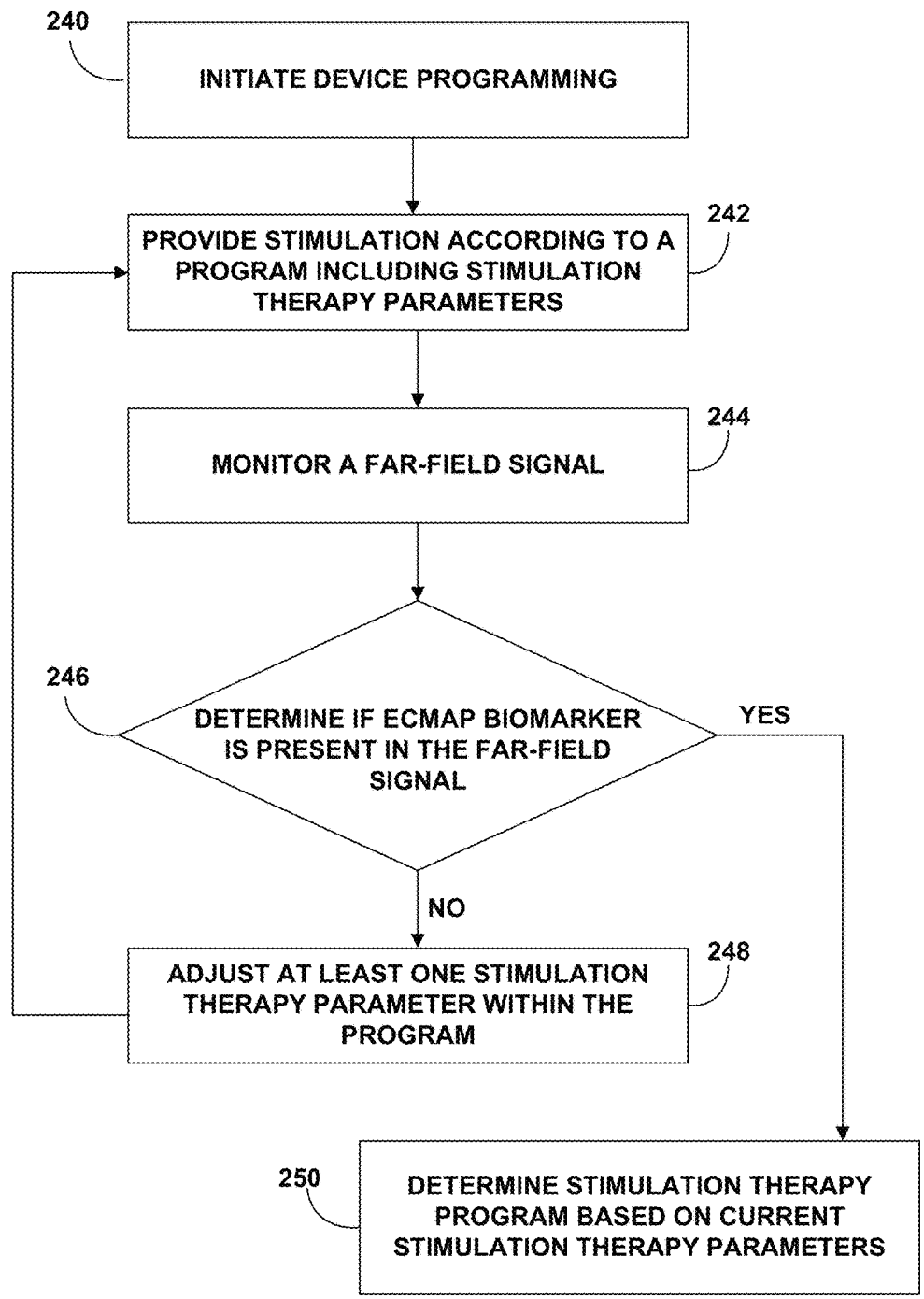
FIG. 13 is a flow diagram illustrating an example technique for adjusting electrical stimulation therapy parameters consistent with this disclosure.

FIG. 13 is a flow diagram illustrating an example technique consistent with the present disclosure. Although discussed with respect to system 10 of FIG. 1, the technique of FIG. 13 may be implemented, at least in part, by system 22 of FIG. 2. In some examples, device programming may be initiated automatically by IMD 14. For example, device programming may occur at regular intervals, such as daily, weekly or monthly. System 10 initiates device programming (240). In some examples, IMD 14 may automatically initiate programming in response to a detection by posture state module 86 that the posture of patient 12 has changed. In some examples, external programmer 20 may initiate device programming (240). For example, a clinician may do initial programming of IMD 14 while patient 12 is in the office, or follow-up programming during a follow-up visit by patient 12.

Once device programming has been initiated, IMD 14 provides stimulation according to a therapy program including a set of stimulation therapy parameters (242). In some examples, the therapy program may be the therapy program currently being used by IMD 14 to provide stimulation therapy to patient 12. In some examples, the therapy program may be an initial therapy program used to start device programming. The initial therapy program may include base values for electrode location, stimulation pulse width, stimulation frequency, and stimulation amplitude, for example.

IMD 14 then monitors a far-field signal (244) using eCMAP sensor 92. In some examples, the far-field signal is collected from electrodes in approximately the same location as the electrodes providing stimulation. In some examples, the far-field signal is collected using the same electrodes as the ones providing stimulation. eCMAP sensor 92 and/or processor 80 determines if an eCMAP biomarker is present in the far-field signal (246). In some examples, determining if an eCMAP biomarker is present in the far-field signal may include determining if a desired eCMAP biomarker is present. Detection of the eCMAP biomarker may include capturing a far-field signal for a predetermined amount of time after the application of the stimulation pulse. In some examples, processor 80 analyzes the detected eCMAP biomarker. Analysis may include, determining if an eCMAP biomarker is present in the signal, determining the time between the application of the stimulation pulse and the receipt of the eCMAP biomarker by eCMAP sensor 92, determining the amplitude of the eCMAP biomarker, or comparing the detected signal to a template of a desired eCMAP biomarker, for example. Based on the detection and/or analysis of the far-field signal, processor 80 determines if an eCMAP biomarker is present in the far-field signal (246). For example, an eCMAP biomarker is present and/or the desired eCMAP biomarker is present, then IMD 14 determines a stimulation therapy program based on the current simulation therapy parameters (250). In some examples, IMD 14 creates a stimulation therapy program where one or more of the stimulation therapy parameters is at a different value than was in the stimulation therapy that resulted in the detected eCMAP biomarker. For example, the stimulation therapy program may provide stimulation at an intensity of approximately 50-90% of the stimulation intensity that resulted in the eCMAP biomarker being detected. Stimulation intensity may be adjusted by adjusting the amplitude, frequency and/or pulse width of stimulation pulses.

In some examples, the initial therapy program may not be the first therapy program that has been used by IMD 14, but rather a therapy program used going forward until the next time device programming is initiated. If an eCMAP biomarker is not present or does not correspond to the desired outcome, then processor 80 adjusts at least one stimulation therapy parameter within the therapy program (248). For example, if analysis of the far-field signal indicates that the therapy program does not result in activation of the muscle action potential, then the total intensity of the stimulation therapy pulse may be increased. This may include increasing the amplitude of the stimulation pulse, the length of the stimulation pulse, the pulse rate, or a combination of these parameters. Stimulation generator 84 provides stimulation according to the updated therapy program (242). The process of providing stimulation (242), monitoring a far-field signal (244), analyzing the far-field signal to determine if an eCMAP biomarker is present (246) and/or corresponds to a desired outcome is repeated, until the eCMAP biomarker is present/and or corresponds to the desired outcome.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The following examples describe one or more aspects of the disclosure.

Example 1

A method comprising: applying, via one or more electrodes, stimulation therapy to a patient according to a set of stimulation therapy parameters; detecting a signal including an evoked compound muscle action potential (eCMAP) in response to the application of the stimulation therapy; and adjusting one or more of the stimulation parameters based on the detected signal.

Example 2

The method of example 1, further comprising detecting the signal via the one or more electrodes.

Example 3

The method of any of examples 1-2, further comprising: detecting a change in patient posture from a first posture state to a second posture state; and in response to detection of the change in patient posture, detecting a second signal including the eCMAP in response to the application of the stimulation therapy.

Example 4

The method of any of examples 1-3, further comprising: responsive to detecting the change in patient posture, applying the stimulation therapy according to a second set of stimulation therapy parameters associated with the second posture state; detecting the second signal including the eCMAP in response to the application of stimulation therapy according to the second set of stimulation therapy parameters; and adjusting one or more of the stimulation parameters of the second set of stimulation parameters based on the detected signal.

Example 5

The method of any of examples 1-4, further comprising storing a third set of stimulation parameters including the one or more adjusted stimulation parameters in association with the detected patient posture.

Example 6

The method of any of examples 1-5, further comprising: comparing one or more characteristics of the detected eCMAP to one or more corresponding characteristics of a reference eCMAP; adjusting one or more of the stimulation parameters based on the comparison; and applying the stimulation therapy based on an adjusted set of stimulation therapy parameters.

Example 7

The method of any of examples 1-6, wherein the reference eCMAP is a stored eCMAP.

Example 8

The method of any of examples 1-7, further comprising detecting the signal including the eCMAP in response to the application of the stimulation therapy at a predetermined interval.

Example 9

The method of any of examples 1-8, further comprising: administering a muscle paralytic; applying, via one or more electrodes, the stimulation therapy to the patient according to the set of stimulation therapy parameters; detecting a second signal; confirming the first detected signal is an eCMAP signal based on the second signal.

Example 10

The method of any of examples 1-9, wherein the signal is a far-field signal.

Example 11

The method of any of examples 1-10, wherein applying stimulation therapy to the patient comprises applying stimulation therapy to a sacral nerve of the patient.

Example 12

The method of any of examples 1-11, wherein detecting the signal including the evoked compound muscle action potential (eCMAP) comprises detecting a far-field signal.

Example 13

The method of any of examples 1-12, wherein detecting the signal including the evoked compound muscle action potential (eCMAP) comprises detecting a far-field signal via one or more electrodes located in the levator ani of the patient.

Example 14

A system comprising: a stimulation generator; one or more electrodes configured to apply stimulation therapy from the stimulation generator based on a set of stimulation therapy parameters; and a processor configured to: receive a detected signal including an evoked compound muscle action potential (eCMAP) in response to the application of the stimulation therapy: analyze the detected signal; and adjust at least one of the stimulation parameters based on the analysis of the detect signal.

Example 15

The system of example 14, wherein the signal is detected via at least one electrode of the one or more electrodes.

Example 16

The system of any of examples 14-15, further comprising: a posture state module configured to detect a posture state; and wherein the processor is further configured to detect a change in the posture state from a first posture state to a second posture state, and in response to detection of the change in patient posture from the first posture state to the second posture state, detect the signal including an eCMAP in response to the application of the stimulation therapy.

Example 17

The system of any of examples 14-16, further comprising: wherein the one or more electrodes are further configured to provide stimulation according to a second set of stimulation therapy parameters associated with the second posture state; and wherein the processor is further configured to: detect the signal including an eCMAP in response to the application of stimulation therapy according to the second set of stimulation therapy parameters; and adjust at least one of the stimulation parameters of the second set of stimulation parameters.

Example 18

The system of any of examples 14-17, further comprising a memory configured to store stimulation parameters, wherein the processor is configured to generate a third set of stimulation parameters including the one or more adjusted stimulation parameters in association with the change in posture state, and stores the third set of stimulation parameters in the memory.

Example 19

The system of any of examples 14-18, wherein the processor is further configured to: compare one or more characteristics of the detected eCMAP to one or more corresponding characteristics of a reference eCMAP; adjust at least one of the stimulation parameters based on the comparison; and wherein the one or more electrodes are further configured to provide stimulation therapy based on an adjusted set of stimulation therapy parameters.

Example 20

The system of any of examples 14-19, wherein the processor is further configured to detect the signal including an eCMAP in response to the application of the stimulation therapy at a predetermined interval.

Example 21

The system of any of examples 14-20, further comprising a memory configure to store the set of stimulation parameters including the at least one adjusted stimulation parameter.

Example 22

The system of any of examples 14-21, wherein the one or more electrodes is further configured to detect a far-field signal.

Example 23

The system of any of examples 14-22, wherein the one or more electrodes are further configured to apply the stimulation therapy to a sacral nerve of a patient.

Example 24

The system of any of examples 14-23, wherein the processor configured receive the detected signal including the evoked compound muscle action potential (eCMAP) in response to the application of the stimulation therapy by receiving a signal sensed as a far-field signal.

Example 25

A system comprising: means for applying stimulation therapy to a patient according to a set of stimulation therapy parameters; means for detecting a signal including an evoked compound muscle action potential (eCMAP) in response to the application of the stimulation therapy; and means for adjusting one or more of the stimulation parameters based on the detected signal.

Example 26

The system of example 25, wherein the means for applying stimulation therapy to the patient comprises means for applying stimulation therapy to a nerve of the patient at a first location; and wherein the means for detecting the signal including the eCMAP comprises means for detecting a far-field signal.

Example 27

The system of any of examples 25-26, wherein the means for applying stimulation therapy to the nerve of the patient comprises means for applying stimulation therapy to a sacral nerve of the patient.

Example 28

The system of any of examples 25-27, wherein the means for detecting the signal including the eCMAP comprises means for detecting the signal as the far-field signal from the levator ani of the patient.

Various examples consistent with this disclosure have been described. These and other examples are within the scope of the following claims.

What is claimed is:
1. A method comprising:
applying, via one or more electrodes, stimulation therapy to a patient according to a set of stimulation therapy parameters;
detecting, using at least one electrode of the one or more electrodes used for applying the stimulation therapy to the patient, a signal including an evoked compound muscle action potential (eCMAP) in response to the application of the stimulation therapy;
detecting, using a posture state module, a posture state of the patient; and adjusting, by a processor, one or more stimulation therapy parameters of the set of stimulation therapy parameters based on the detected signal and the detected posture state.

2. The method of claim 1, further comprising detecting the signal via a same set of the one or more electrodes used for applying the stimulation therapy to the patient.

3. The method of claim 1, further comprising:
detecting a change in the posture state of the patient from a first posture state to a second posture state; and
in response to detection of the change in the posture state, detecting a second signal including the eCMAP in response to the application of the stimulation therapy.

4. The method of claim 3, further comprising:
responsive to detecting the change in the posture state, applying the stimulation therapy according to a second set of stimulation therapy parameters associated with the second posture state;
detecting the second signal including the eCMAP in response to the application of stimulation therapy according to the second set of stimulation therapy parameters; and
adjusting one or more stimulation therapy parameters of the second set of stimulation therapy parameters based on the detected signal.

5. The method of claim 4, further comprising storing a third set of stimulation therapy parameters including the one or more stimulation therapy parameters of the second set of stimulation therapy parameters adjusted in association with the detected change in the posture state.

6. The method of claim 1, further comprising:
comparing one or more characteristics of the detected eCMAP to one or more corresponding characteristics of a reference eCMAP;
adjusting one or more stimulation therapy parameters of the set of stimulation therapy parameters based at least in part on the comparison; and
applying the stimulation therapy according to the set of stimulation therapy parameters adjusted based at least in part on the comparison.

7. The method of claim 6, wherein the reference eCMAP is a stored eCMAP.

8. The method of claim 1, further comprising detecting the signal including the eCMAP in response to the application of the stimulation therapy at a predetermined interval.

9. The method of claim 1, further comprising:
applying, via one or more electrodes and in response to a muscle paralytic being administered, the stimulation therapy to the patient according to the set of stimulation therapy parameters;
detecting a second signal; and
confirming the first detected signal is an eCMAP signal based on the second signal.

10. The method of claim 1, wherein the signal is a far-field signal.

11. The method of claim 1, wherein applying stimulation therapy to the patient comprises applying stimulation therapy to a sacral nerve of the patient.

12. The method of claim 11, wherein detecting the signal including the evoked compound muscle action potential (eCMAP) comprises detecting a far-field signal.

13. The method of claim 12, wherein detecting the signal including the evoked compound muscle action potential (eCMAP) comprises detecting a far-field signal via one or more electrodes located in a levator ani of the patient.

14. A system comprising:
a posture state module configured to detect a posture state;
a stimulation generator;
one or more electrodes configured to apply stimulation therapy from the stimulation generator based on a set of stimulation therapy parameters; and
a processor configured to:
receive, using at least one electrode of the one or more electrodes configured to apply the stimulation therapy, a detected signal including an evoked compound muscle action potential (eCMAP) in response to the application of the stimulation therapy;
receive, from the posture state module, an indication of the detected posture state;
analyze the detected signal; and
adjust at least one stimulation therapy parameter of the set of stimulation therapy parameters based on the analysis of the detected signal and the indication of the detected posture state.

15. The system of claim 14, wherein the signal is detected via a same set of the one or more electrodes configured to apply the stimulation therapy.

16. The system of claim 14,
wherein the processor is further configured to detect a change in the posture state from a first posture state to a second posture state based on the indication received from the posture state module, and in response to detection of the change in posture state of the patient from the first posture state to the second posture state, detect the signal including an eCMAP in response to the application of the stimulation therapy.

17. The system of claim 16, further comprising:
wherein the one or more electrodes are further configured to provide stimulation according to a second set of stimulation therapy parameters associated with the second posture state; and
wherein the processor is further configured to:
detect the signal including an eCMAP in response to the application of stimulation therapy according to the second set of stimulation therapy parameters; and
adjust at least one stimulation therapy parameter of the second set of stimulation therapy parameters based at least in part on the detected signal.

18. The system of claim 17, further comprising a memory configured to store stimulation parameters, wherein the processor is configured to generate a third set of stimulation therapy parameters including the at least one stimulation therapy parameter of the second set of stimulation therapy parameters adjusted based on the detected signal in association with the change in posture state, and store the third set of stimulation parameters in the memory.

19. The system of claim 14, wherein the processor is further configured to:
compare one or more characteristics of the detected eCMAP to one or more corresponding characteristics of a reference eCMAP;
adjust at least one stimulation therapy parameter of the set of stimulation therapy parameters based at least in part on the comparison; and
wherein the one or more electrodes are further configured to provide stimulation therapy based on the set of stimulation therapy parameters adjusted based on the comparison.

20. The system of claim 14, wherein the processor is further configured to detect the signal including an eCMAP in response to the application of the stimulation therapy at a predetermined interval.

21. The system of claim 14, further comprising a memory configured to store the set of stimulation therapy parameters including the at least one stimulation therapy parameter adjusted based on the analysis.

22. The system of claim 14, wherein the one or more electrodes is further configured to detect a far-field signal.

23. The system of claim 14, wherein the one or more electrodes are further configured to apply the stimulation therapy to a sacral nerve of a patient.

24. The system of claim 23, wherein the processor is configured to receive the detected signal including the evoked compound muscle action potential (eCMAP) in response to the application of the stimulation therapy by receiving a signal sensed as a far-field signal.

25. A system comprising:
  means for applying, through one or more electrodes, stimulation therapy to a patient according to a set of stimulation therapy parameters;
  means for detecting, using at least one electrode of the one or more electrodes used for applying the stimulation therapy, a signal including an evoked compound muscle action potential (eCMAP) in response to the application of the stimulation therapy;
  means for detecting a posture state of the patient; and
  means for adjusting one or more stimulation therapy parameter of the set of stimulation therapy parameters based on the detected signal and the detected posture state.

26. The system of claim 25, wherein the means for applying stimulation therapy to the patient comprises means for applying stimulation therapy to a nerve of the patient at a first location; and wherein the means for detecting the signal including the eCMAP comprises means for detecting a far-field signal.

27. The system of claim 26, wherein the means for applying stimulation therapy to the nerve of the patient comprises means for applying stimulation therapy to a sacral nerve of the patient.

28. The system of claim 27, wherein the means for detecting the signal including the eCMAP comprises means for detecting the signal as the far-field signal from a levator ani of the patient.

* * * * *